United States Patent
Andoh et al.

(10) Patent No.: US 9,347,881 B2
(45) Date of Patent: May 24, 2016

(54) DEVICE AND METHOD FOR DETECTING STATE OF DISCHARGED LIQUID DROPLET AND IMAGE FORMING DEVICE INCORPORATING SUCH DEVICE

(71) Applicants: Hiroshi Andoh, Ibaraki (JP); Hideharu Miki, Ibaraki (JP); Genichiro Kawamichi, Ibaraki (JP); Shigeru Morinaga, Kanagawa (JP); Kohji Tokuyama, Ibaraki (JP); Toshihide Inaba, Tokyo (JP); Mitsuyuki Karasawa, Ibaraki (JP); Takeo Shirato, Ibaraki (JP)

(72) Inventors: Hiroshi Andoh, Ibaraki (JP); Hideharu Miki, Ibaraki (JP); Genichiro Kawamichi, Ibaraki (JP); Shigeru Morinaga, Kanagawa (JP); Kohji Tokuyama, Ibaraki (JP); Toshihide Inaba, Tokyo (JP); Mitsuyuki Karasawa, Ibaraki (JP); Takeo Shirato, Ibaraki (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/577,105

(22) Filed: Dec. 19, 2014

(65) Prior Publication Data
US 2015/0177136 A1 Jun. 25, 2015

(30) Foreign Application Priority Data
Dec. 20, 2013 (JP) .................. 2013-264596

(51) Int. Cl.
*G01N 21/00* (2006.01)
*G01N 21/49* (2006.01)
*G01N 21/47* (2006.01)

(52) U.S. Cl.
CPC ............. *G01N 21/49* (2013.01); *G01N 21/47* (2013.01); *G01N 2021/4707* (2013.01); *G01N 2021/4769* (2013.01)

(58) Field of Classification Search
CPC .... B41J 2/04586; B41J 2/16579; B41J 2/195; B41J 2/04561; B41J 2/125; B41J 2/0451; G01N 2021/4769; G01N 21/49; G01N 21/47; B01N 2021/4707
USPC ..................... 356/335–343; 347/19
See application file for complete search history.

(56) References Cited

U.S. PATENT DOCUMENTS

| | | | |
|---|---|---|---|
| 8,485,633 B2* | 7/2013 | Ito ............... | B41J 2/04561 347/19 |
| 8,870,335 B2* | 10/2014 | Andoh ............ | B41J 2/195 347/19 |
| 2004/0196319 A1* | 10/2004 | Aruga ............. | B41J 2/0451 347/9 |

(Continued)

FOREIGN PATENT DOCUMENTS

| JP | 2008-162148 | 7/2008 |
|---|---|---|
| JP | 2014-117809 | 6/2014 |

*Primary Examiner* — Hoa Pham
(74) *Attorney, Agent, or Firm* — Duft Bornsen & Fettig LLP

(57) ABSTRACT

A device for detecting a state of a liquid droplet discharged from each of nozzles placed in one or more rows, includes a light emitting element to emit a light beam to the liquid droplet from a nozzle in question, and a pair of light receiving elements disposed on both sides of a beam diameter of the light beam via an optical axis to receive scattered light occurring from the liquid droplet for detecting a state of the discharged liquid droplet on the basis of the scattered light. Either of the pair of the light receiving elements is selected for receiving the scattered light from the liquid droplet discharged from the nozzle according to a positional relation between the nozzle and the pair of light receiving elements.

16 Claims, 18 Drawing Sheets

(56) References Cited

U.S. PATENT DOCUMENTS

| | | | |
|---|---|---|---|
| 2009/0115812 A1* | 5/2009 | Ito | B41J 2/2142 347/19 |
| 2009/0141057 A1* | 6/2009 | Hayashi | B41J 2/2142 347/9 |
| 2013/0077099 A1* | 3/2013 | Mochizuki | G01N 21/49 356/445 |
| 2015/0009252 A1* | 1/2015 | Andoh | B41J 2/2142 347/9 |
| 2015/0290929 A1* | 10/2015 | Ando | B41J 2/0451 347/9 |

* cited by examiner

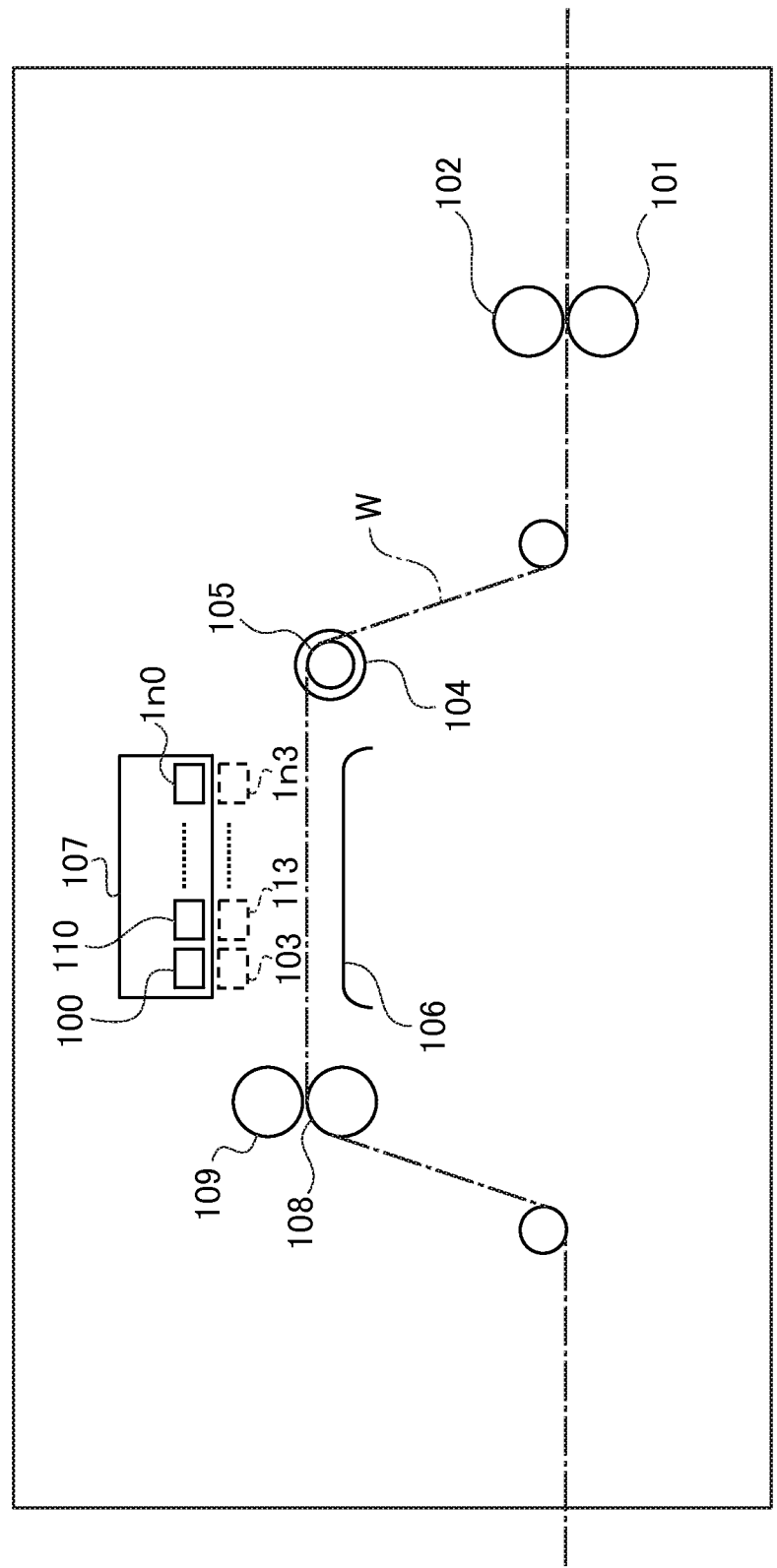

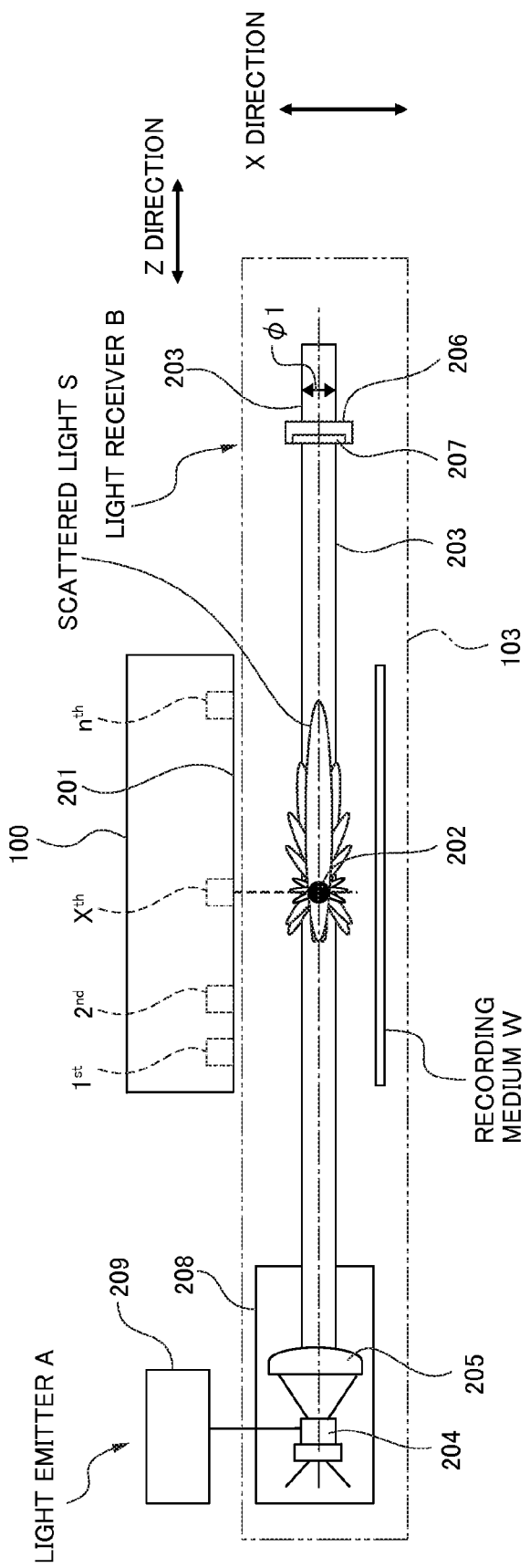

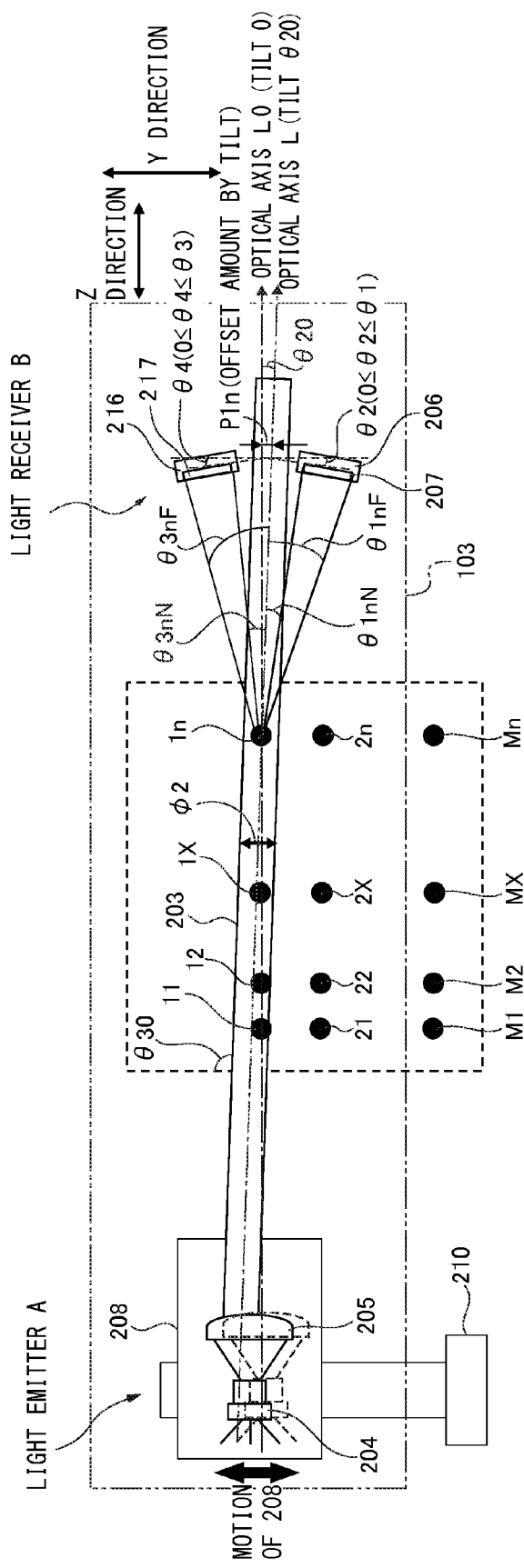

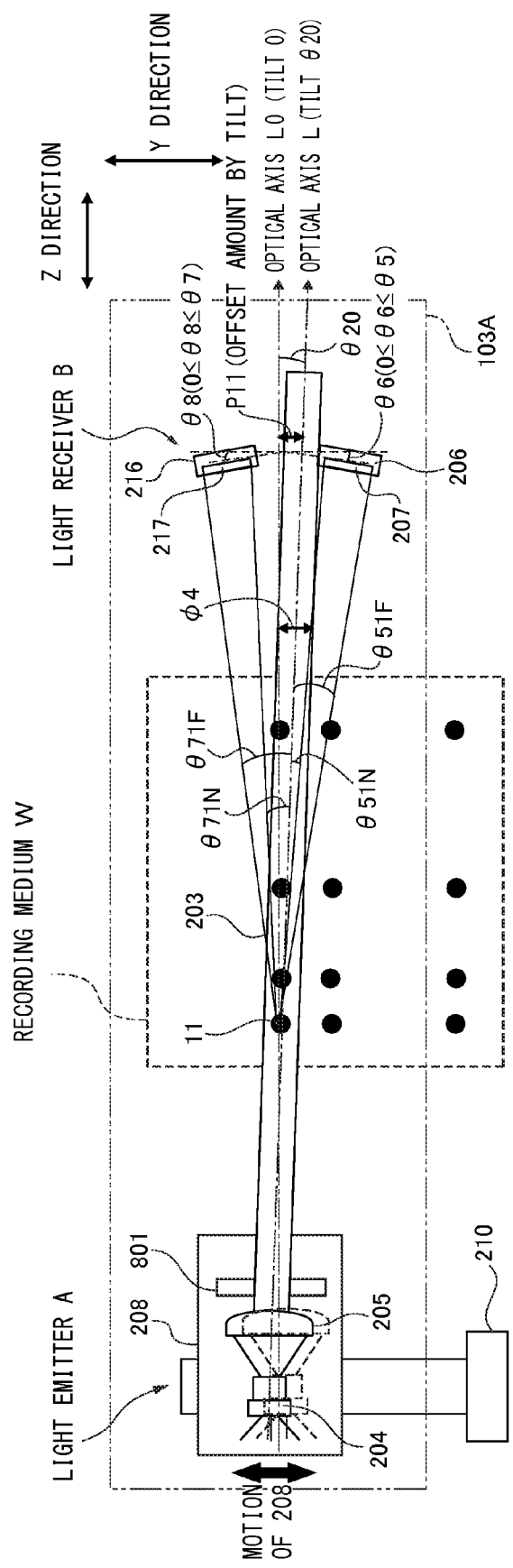

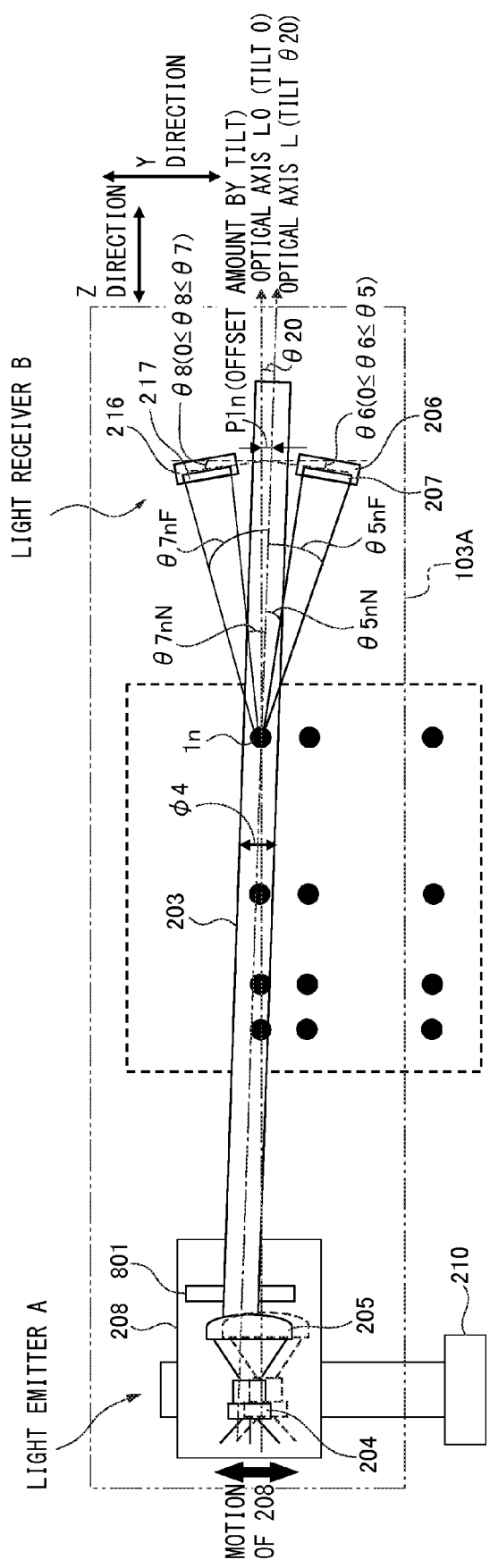

DEVICE AND METHOD FOR DETECTING STATE OF DISCHARGED LIQUID DROPLET AND IMAGE FORMING DEVICE INCORPORATING SUCH DEVICE

CROSS REFERENCE TO RELATED APPLICATION

The present application is based on and claims priority from Japanese Patent Application No. 2013-264596, filed on Dec. 20, 2013, the disclosure of which is hereby incorporated by reference in its entirety.

BACKGROUND OF THE INVENTION

1. Field of the Invention

The present invention relates to device and method for detecting a state of liquid droplets discharged from nozzle holes of a recording head as well as to an image forming device such as a printer, copier, or facsimile machine incorporating such a device.

2. Description of the Related Art

In general a serial type image forming device and a line type image forming device are known. The serial-type image forming device forms an image by a recording head's discharging liquid droplets while moving in a main scanning direction. The line-type image forming device uses a line head to discharge liquid droplets without moving. Because of forming images by discharging liquid droplets, the image quality of these image forming devices deteriorates if the level of nozzle discharge is degraded due to an increase in ink viscosity and ink solidification arising from evaporation of solvent from nozzles, dust attachment, bubble interfusion or else.

In view of this, Japanese Patent No. 4925184 discloses a device for detecting the state of liquid droplets discharged from a recording head, for example. This device is a forward scattered light type which emits a laser beam from one side of a nozzle row of a recording head along the nozzle row and receives scattered light from the liquid droplets on a light receiving element placed on the other side of the nozzle row aside from the optical axis of the light beam, to thereby determine presence or absence of a discharged liquid droplet. In this document a single light receiving element is provided for one or more nozzle rows.

Further, aiming for accurately detecting a state of discharged fluid such as ink droplets with a less complicated structure at low cost, the above document discloses, for example, a structure that light receiving elements are disposed at two more separate locations off the optical axis of a light beam from the light emitting element, to be able to receive scattered light and detect an ink discharged state from a difference in the optical output values of the light receiving elements.

However, the related-art technique disclosed in the above document has a problem that when the optical axis of the light beam is tilted toward the light receiving elements and made aligned with liquid droplets closer to the light emitting element for detection, the optical axis becomes closer to the light receiving elements positioned as above so that amount of offset light (noise light) including a part of the light beam or reflected light is increased. Due to the increase in the offset light amount, the received light amount exceeds a saturation limit value of a detection circuit, making it difficult to detect a state of discharged liquid droplets. Meanwhile, when the optical axis of the light beam is tilted to the opposite side of the light receiving elements and made aligned with liquid droplets closer to the light receiving elements for detection, the optical axis becomes further from the light receiving elements positioned as above. Because of this, the amount of received scattered light does not reach a detectable threshold, making it difficult to detect a state of discharged liquid droplets.

SUMMARY OF THE INVENTION

The present invention aims to provide a device which can accurately detect a state of liquid droplets discharged from nozzles in one or more rows with a light beam even when the optical axis of the light beam is tilted.

According to one embodiment, a device for detecting a state of a liquid droplet discharged from each of nozzles placed in one or more rows, comprises a light emitting element to emit a light beam to the liquid droplet from a nozzle in question, and a pair of light receiving elements disposed on both sides of a beam diameter of the light beam via an optical axis to receive scattered light occurring from the liquid droplet for detecting a state of the discharged liquid droplet on the basis of the scattered light, wherein either of the pair of the light receiving elements is selected for receiving the scattered light from the liquid droplet discharged from the nozzle according to a positional relation between the nozzle and the pair of light receiving elements.

BRIEF DESCRIPTION OF THE DRAWINGS

Features, embodiments, and advantages of the present invention will become apparent from the following detailed description with reference to the accompanying drawings:

FIG. 1 schematically shows the structure of a fluid discharge recording type image forming device comprising a discharged liquid droplet detecting device according to a first embodiment;

FIG. 2A is a schematic side view of an inkjet head and the discharged liquid droplet detecting device according to the first embodiment by way of example;

FIG. 2C is a schematic overhead view of the discharged liquid droplet detecting device according to the first embodiment by way of example;

FIG. 10B is a schematic overhead view of the discharged liquid droplet detecting device according to the second embodiment by way of example;

FIG. 10C is a schematic overhead view of the discharged liquid droplet detecting device according to the second embodiment by way of example;

DETAILED DESCRIPTION OF THE PREFERRED EMBODIMENT

Hereinafter, embodiments of the present invention will be described in detail with reference to the accompanying drawings.

Figure 2B:
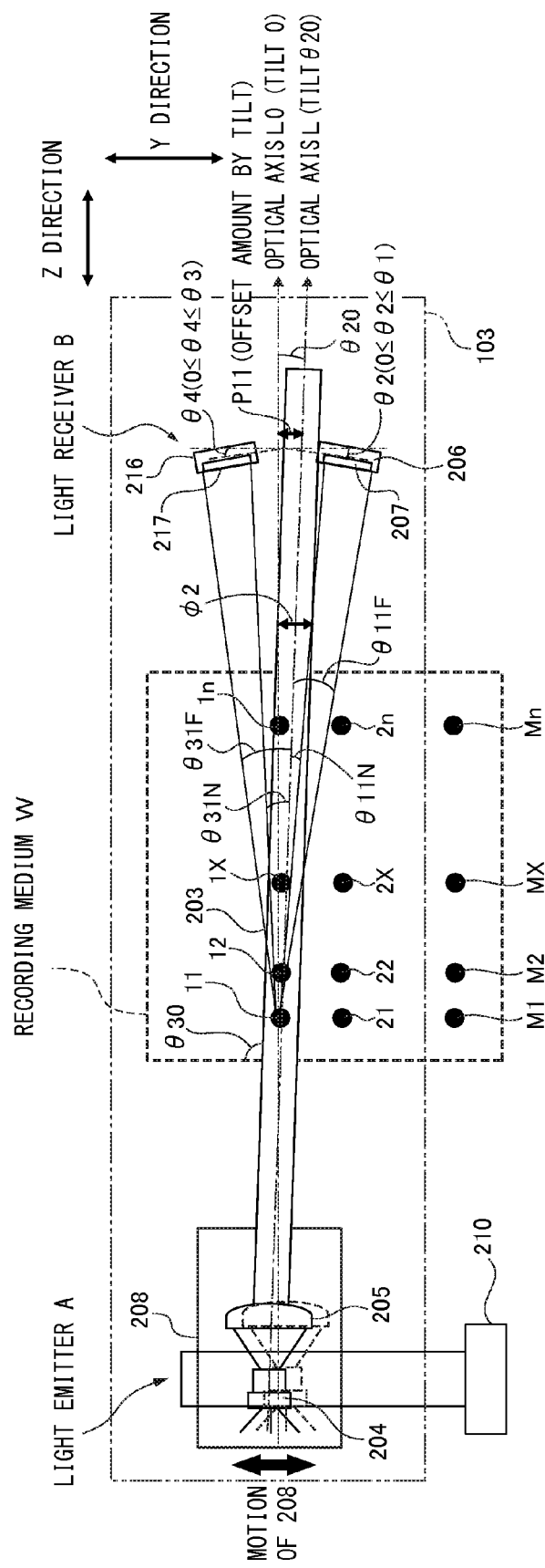
FIG. 2B is a schematic overhead view of the discharged liquid droplet detecting device according to the first embodiment by way of example.

As shown in FIG. 2A to FIG. 2C, a discharged liquid droplet detecting device 103 according to one embodiment is intended to detect a state of an ink droplet 202 discharged from each nozzle of one or more nozzle rows according to scattered light S which occurs when a light beam 203 hits the ink droplet 202. This device 103 comprises a light emitting element 204 to emit the light beam 203 and a pair of light receiving elements 206, 216 disposed on both sides of the light beam 203 in diameter of $\phi 2$ via an optical axis L to receive the scattered light S from the ink droplet 202. It selects one of the light receiving elements 206, 216 to receive the scattered light S from the ink droplet 202 from one of the nozzles on the basis of a positional relationship between the nozzle in question and the light receiving elements 206, 216.

Now, the positions of the nozzle and light receiving elements relative to the amount of scattered light from ink droplets are described. Amount of scattered light from ink droplets received by a light receiving element depends on a distance between a nozzle in question and the light receiving element and a scattering angle of the scattered light, and tends to attenuate as a quadratic function relative to the distance and attenuate as a logarithmic function relative to the scattering angle. The scattered light amount from an ink droplet discharged from a nozzle on a light emitting element side, that is, in a larger distance or far from the light receiving element shows a large attenuation rate by the distance and a small attenuation rate by the scattering angle. Thus, the attenuation rate decreases mainly by the distance. Meanwhile, the scattered light amount from an ink droplet discharged from a nozzle on a light receiving element side, that is, in a smaller distance from or close to the light receiving element shows a small attenuation rate by the distance and a large attenuation rate by the scattering angle. Thus, the attenuation rate decreases mainly by the scattering angle.

Further, for decreasing the amount of offset light or noise light such as reflected light and a part of the light beam other than the scattered light, it is necessary to provide a certain distance between the light beam and the light receiving element. Therefore, the scattered light amount by the ink droplet from the nozzle on the light receiving element side is smaller than that by the ink droplet from the nozzle on the light emitting element side.

Moreover, when the optical axis of the light beam is tilted, the distances from the two light receiving elements to the light beam differ. The light receiving element further from the light beam or in a larger distance receives a smaller amount of scattered light from an ink droplet while that closer to the light beam or in a smaller distance receives a larger amount of scattered light from an ink droplet.

Moreover, the amount of offset light or noise light depends on the distance between the light beam and light receiving element. With an inclination of the optical axis of the light beam, the light receiving element closer to the light beam receives a larger amount of offset light while that further from the light beam receives a smaller amount of offset light. The amount of offset (relative to the light beam with no tilt) of the light beam caused by a tilt of the optical axis differs depending on a distance from the ink droplet to the light receiving element. The offset amount of the light beam is large at the ink droplet from a nozzle closer to the light emitting element due to a large distance to the light receiving element and it is small at the ink droplet from a nozzle closer to the light receiving element due to a short distance. Thus, for detecting an ink droplet from a nozzle on the light emitting element side, the light receiving element closer to the light beam receives a larger offset light amount and the one further from the light beam receives a smaller offset light amount than for detecting an ink droplet from a nozzle on the light receiving element side.

In view of the above, according to the discharged liquid droplet detecting device 103 the light receiving elements 206, 216 are provided on both sides of the diameter $\phi 2$ of the light beam 203 to detect the scattered light S from the ink droplet 202. Further, the light receiving element to receive the scattered light S is selectively changed depending on a positional relationship between a nozzle as a subject of detection and the light receiving elements 206, 216. This makes it possible to accurately detect the scattered light S from the ink droplet 202 with a selected one of the light receiving elements 206, 216 even if the optical axis L of the light beam 203 is tilted due to a tilt of the light emitting element or a lens (later-described collimator lens 205) or there is a nozzle misaligned from the nozzle row. Accordingly, it is able to accurately determine a state of discharged liquid droplets.

According to one embodiment the light receiving element further from the light beam 203, for example, the light receiving element 216 is selected for detecting scattered light S from the ink droplet 202 closer to the light emitting element 201 which is far from the light receiving elements 206, 216. The light receiving element 216 is the one to detect so that the offset light amount will not exceed a saturation limit value and the scattered light amount will be a detectable threshold or more. Accordingly, it is able to precisely detect the scattered light S from the ink droplet 202 and accurately determine the discharged state of the ink droplet.

Meanwhile, for detecting the ink droplet 202 from a nozzle close to the light receiving elements 206, 216, one of the light receiving elements 206, 216 (for example, 206) closer to the light beam 203 is selected. By detecting with the light receiving element 206, the offset light amount will not exceed a saturation limit value and the scattered light amount will be or exceed a detectable threshold. Accordingly, it is able to precisely detect the scattered light S from the ink droplet 202 and accurately determine the discharged state of the ink droplet.

First Embodiment

Now, a discharged liquid droplet detecting device according to a first embodiment and an image forming device comprising this device is described referring to the accompanying drawings. Wherever possible, the same reference numbers will be used throughout the drawings to refer to the same or like parts, and overlapping descriptions will be omitted or simplified when appropriate. It should be understood that the detailed description and specific examples, while indicating the preferred embodiment of the invention, are intended for purposes of illustration only and are not intended to limit the scope of the invention.

The structure of the image forming device according to the first embodiment is described, referring to FIG. 1. FIG. 1 is a schematic side view of a fluid discharge recording type image forming device (hereinafter, referred to as inkjet printer sometimes).

The image forming device according to the first embodiment in FIG. 1 comprises a paper conveyance roller 101, a paper conveyance driven roller 102, discharged liquid droplet detecting devices 103, 113, ..., 1n3, an encoder 104 to detect a feed amount of a recording medium, a driven roller 105, a plate 106, and an inkjet head array 107 including inkjet heads 100, 110, ..., 1n0, an ejected paper conveyance roller 108 and an ejected paper conveyance driven roller 109. The discharged liquid droplet detecting device 103, 113, ..., 1n3 indicated by a broken line in FIG. 1 are the ones according to the present invention.

In the inkjet printer as configured above, a recording medium W is conveyed by the paper conveyance roller 101 and the paper conveyance driven roller 102 connected to a not-shown paper feed motor from a not-shown paper feeder to the plate 106 through a driven roller 105. The driven roller 105 is driven along with the movement of the recording medium W and includes the encoder 104 which outputs a detection signal in accordance with movement of the recording medium W in a certain distance.

The inkjet head array 107 is placed to oppose the plate 106 and the inkjet heads 100, 110, ..., 1n0 discharge ink droplets onto the recording medium W on the plate 106. The recording medium W is then conveyed from the plate 106 to outside the inkjet printer by the ejected paper conveyance roller 108 and the ejected paper conveyance driven roller 109 connected to a not-shown paper ejection motor. According to the first embodiment the encoder 104 is placed between the paper conveyance roller 101 and the plate 106. Alternatively, the encoder 104 can be placed between the plate 106 and the ejected paper conveyance roller 108.

Herein, the inkjet printer or discharged fluid recording type image forming device refers to a device to form images by attaching ink onto a medium such as paper, thread, fiber, cloth, leather, metal, plastic, glass, wood, or ceramics. Also, image forming refers to generating not only a meaningful image as text or graphic on a medium but also a meaningless image as pattern, that is, merely attaching liquid droplets onto a medium.

Further, ink is not limited to a material called ink and used as a general term for all kinds of fluids usable in image forming such as recording fluid, fixing solution, resin, liquid. Paper is not limited to a paper material and used as a general term for materials on which ink droplets are attached, including an OHP sheet, a cloth, a recording medium, and a recording paper. Further, image is not limited to a planar image and includes an image attached to a cubic object and a three-dimensional image of a cubic object.

Figure 2D:
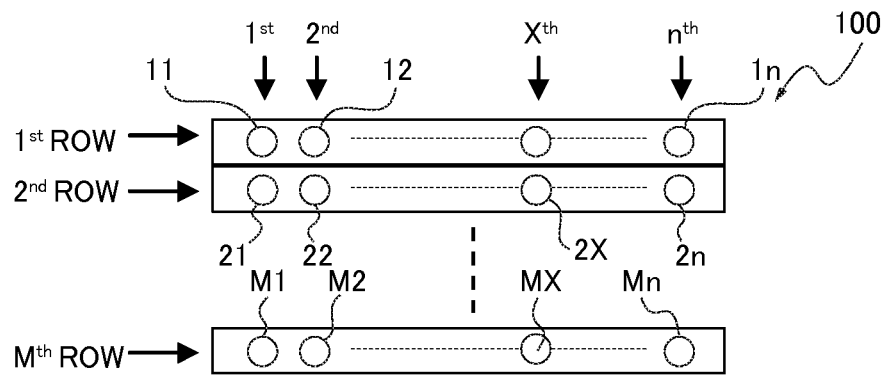
FIG. 2D is a schematic overhead semi-cross section view of the inkjet head according to the first embodiment by way of example.

The structure of the discharged liquid droplet detecting device 103 of the inkjet printer is described, referring to FIG. 2A to FIG. 2D. FIG. 2A is a schematic side view of the inkjet head 100 and the discharged liquid droplet detecting device 103. FIG. 2B is a schematic view of the discharged liquid droplet detecting device 103 as seen from above (inkjet head 100) when the optical axis L of the light beam 203 is aligned with an ink droplet 202 discharged from a first nozzle 11 of a first row and FIG. 2C is the same when the optical axis L of the light beam 203 is aligned with an ink droplet 202 discharged from a $n^{th}$ nozzle 1n of a first row. FIG. 2D is an overhead semi-cross section view of the inkjet head 100. The structures of the other discharged liquid droplet detecting devices 113, ..., 1n3 are the same as that of the discharged liquid droplet detecting device 103, and a description thereof is omitted.

Hereinafter, the discharged liquid droplet detecting device 103 according to the first embodiment is described in detail. The discharged liquid droplet detecting device 103 comprises a light emitter A, a light receiver B and, a moving unit 210 as a mover in FIG. 2A. The light emitter A and light receiver B are disposed such that the optical axis L of the light beam 203 is vertical (Z-direction in FIG. 2B) to a direction (X-direction indicated by a broken-line arrow in FIG. 2B) in which the ink droplet 202 is discharged from a nozzle (11, 12, ..., 1X, ..., 1n) of a nozzle plane 201 of the inkjet head 100. As shown in FIG. 2A to FIG. 2C, the discharged liquid droplet detecting device 103 further comprises a light emitting unit 208 incorporating the light emitter A, the moving unit 210 to move the light emitting unit 208, and a light emission driver 209 to set an emission amount of the light emitting element 204. In FIG. 2B and FIG. 2C the sign, "●" is added with the reference codes, 11, 12, ..., Mn, however, the sign, "●" represents the ink droplet 202 discharged from each nozzle. Each nozzle is placed on an extension line from each ink droplet 202. This applies to the following drawings in the other embodiments.

In FIG. 2B the optical axis L of the light beam 203 is aligned with the ink droplet 202 discharged from the first nozzle 11 of the first row and in FIG. 2C the optical axis L of the light beam 203 is aligned with the ink droplet 202 discharged from the $n^{th}$ nozzle 1n of the first row. The light emitter A is placed so that the optical axis L makes an angle of θ30 (0≤θ30<360 degrees) with the direction (Y-direction) in which the recording medium W is conveyed in FIG. 2B. The angle θ30 can be arbitrarily set in a range of 0≤θ30<360 degrees, but it is preferable that the light emitter A is disposed to be able to emit the light beam 203 in the direction (Z-direction in FIG. 2B) in which the nozzles are arranged. Thus, the discharged liquid droplet detecting devices 103, 113, . . . , 1n3 (n being integer of one or more) can be properly arranged.

As shown in FIG. 2D, the nozzle array is made of M (1, 2, . . . , M) nozzle rows on the nozzle plane 201 of the inkjet head 100 and each nozzle row includes n (1, 2, . . . , X, . . . , n) nozzles. In the drawing, X, n, and M are integers of one or more. $1^{st}, 2^{nd}, \ldots, x^{th}, \ldots, n^{th}$ nozzles in the first row and the second row represented by the sign "○" are given codes 11, 12, . . . , 1X, . . . , 1n, 21, 22, . . . , 2X, . . . , 2n, respectively. Likewise, the third and following rows are the same and the nozzles in the last row M are given codes M1, M2, . . . , MX, . . . , Mn, respectively.

The light emitter A comprises a light emitting element 204 as a semiconductor laser to emit the light beam 203 and a collimator lens 205 to convert the light beam 203 from the light emitting element 204 to a parallel beam in beam diameters of φ1, φ2. Herein, φ1 and φ2 represent major and minor beam diameters. The light emitting element 204 is not limited to a semiconductor laser and it can be comprised of an LED (Light Emitting Diode), for example. The light emitting element 204 and the collimator lens 205 are incorporated in the light emitting unit 208.

Figure 3:
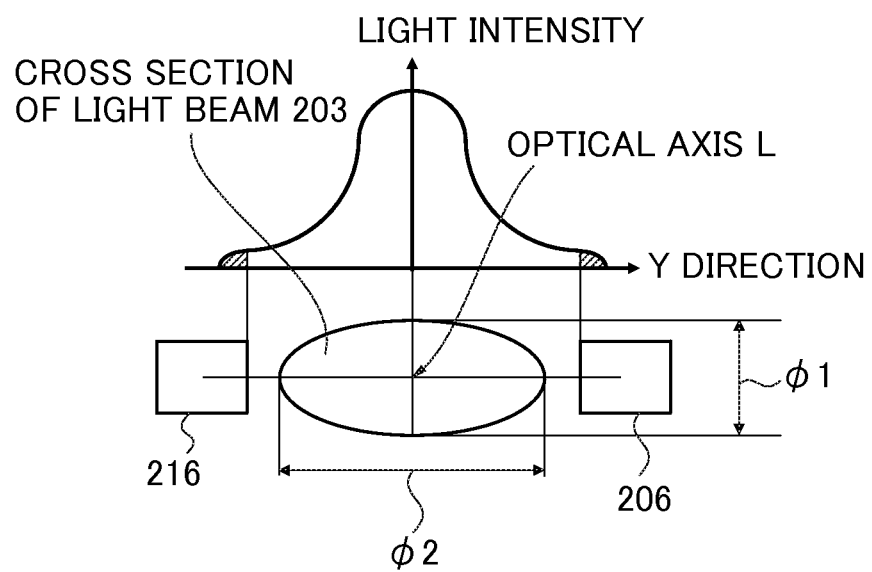
FIG. 3 shows a relationship between intensity distribution of a light beam and each light receiving element when the tilt of the optical axis is zero.

Either of the beam diameters φ1, φ2 can be set to be longer than the other or both of them can be the same (φ1=φ2) depending on various kinds of conditions. Such conditions include the wavelength and intensity distribution of the light beam 203, the interval between the nozzle rows, the shape and size of the ink droplet 202, the type and radiation angle of the light emitting element 204, the distance between the light emitting element 204 and the collimator lens 205, the distance between the light emitting element 204 and the ink droplet 202, the distance between the ink droplet 202 and the light receiving elements 206, 216, the position and size of the light receiving elements 206, 216, and the distance between the inkjet head 100 and a printing material (recording medium W). In the first embodiment φ1 represents the minor axis of the beam and φ2 is the major axis of the beam as shown in FIG. 3.

As shown in FIG. 2B and FIG. 2C, the optical axis L of the light beam 203 is tilted at θ20 (where θ3≤θ20≤θ1) relative to the nozzle rows. The angle θ20 is an angle between the optical axis L0 with no tilt and the optical axis L with tilt relative to the nozzle rows. The angles θ1, θ3 are angles between the two light receiving elements 206, 216 of the light receiver B and optical axis L, respectively. An offset amount P is an offset between the optical axis L0 with no tilt and optical axis L with tilt θ20 relative to the nozzle rows, received by the light receiver B. In FIG. 2B the offset amount when the optical axis L is aligned with the first nozzle of the first row is P1 and in FIG. 2C that when the optical axis L is aligned with the $n^{th}$ nozzle 1n of the first row is P1n.

The moving unit 210 moves the light emitting unit 208 including the light emitter A in a direction crossing the optical axis L of the light beam 203 from the light emitter A. Thereby, the light beam 203 is positioned to irradiate the ink droplet 202 discharged from each nozzle. The moving unit 210 can be, for example, comprised of a drive motor, a gear motor, and a slider pole coupled with the gear motor so that the drive motor drives the gear motor to move the slider pole supporting the light emitting unit 208 upward and downward. The gear motor and slider pole are engaged with a rack provided on the bottom end of the slider pole, for example. However, the moving unit 210 should not be limited to such a configuration and can be any known moving mechanism to be able to move the light emitting unit 208.

Further, with use of the parallel light beam 203 in the first embodiment, the intensity distribution of the light beam 203 is widened and the maximal beam intensity is attenuated due to diffraction as the distance between the light emitting element 204 and the nozzle is lengthened from the closest nozzle 11 to the furthest nozzle 1n. In view of this, according to the first embodiment the light emission driver 209 controls the light emitting element 204 to increase the amount of light emission and the moving unit 210 moves the light emitting unit 208 to a position to optimize the position of the ink droplet 202 and the intensity distribution of the light beam 203. That is, the light emitting unit 208 is moved to a location in which the center of the ink droplet 202 coincides with the position where the intensity distribution of the light beam 203 becomes maximal. This also applies to the following second embodiment.

The light receiver B comprises the pair of light receiving elements 206, 216 each comprising a photodiode. The two light receiving elements 206, 216 are disposed outside (on both sides of) the beam diameter φ2 of the light beam 203 via the optical axis L so that their light receiving surfaces 207, 217 do not enter the beam diameter φ2. Also, they are placed in locations such that their output voltages do not exceed the saturation limit value of offset light, as described later. It is preferable to arrange the light receiving elements 206, 216 in separate positions adjacent to the beam diameter φ2. Moreover, it is preferable to place the light receiving elements 206, 216 symmetrically relative to the optical axis L, that is, in the same distance from the optical axis L.

The light receiving element 206 is disposed at angle θ1 relative to the optical axis L and at angle θ2 (0≤θ2≤θ1) relative to the vertical direction of the optical axis L. The angle θ1 is an angle between the direction in which the ink droplet 202 is discharged from a nozzle in question to the light receiving element 206 and the optical axis L of the light beam 203. The angle θ2 is an angle between the vertical direction of the optical axis L and the light receiving surface 207 of the light receiving element 206.

Now, the angle θ1, represented as θ11N, θ11F in FIG. 2B and 1nN, θ1nF in FIG. 2C, is described in detail. The angle θ11N is an angle between the optical axis L and a direction from the first nozzle 11 of the first nozzle row 1 to one end of the light receiving element 206 close to the nozzle row 1. The angle θ11F is an angle between the optical axis L and a direction from the first nozzle 11 of the first nozzle row 1 to the other end of the light receiving element 206 far to the nozzle row 1. The angle θ1nN is an angle between the optical axis L and a direction from the $n^{th}$ nozzle 1n of the first nozzle row 1 to one end of the light receiving element 206 close to the nozzle row 1. The angle θ1nF is an angle between the optical axis L and a direction from the $n^{th}$ nozzle 1n of the first nozzle row 1 to the other end of the light receiving element 206 far to the nozzle row 1.

The light receiving element 216 is disposed at angle θ3 relative to the optical axis L and at angle θ4 (0≤θ4≤θ3) relative to the vertical direction of the optical axis L. The angle θ3 is an angle between the direction in which the ink droplet 202 is discharged from a nozzle in question to the light receiving element 216 and the optical axis L of the light beam 203. The angle θ4 is an angle between the vertical direction of the optical axis L and the light receiving surface 217 of the light receiving element 216.

Now, the angle θ3, represented as θ31N, θ31F in FIG. 2B and θ3nN, θ3nF in FIG. 2C, is described in detail. The angle θ31N is an angle between the optical axis L and a direction from the first nozzle 11 of the first nozzle row 1 to one end of the light receiving element 216 close to the nozzle row 1. The angle θ31F is an angle between the optical axis L and a direction from the first nozzle 11 of the first nozzle row 1 to the other end of the light receiving element 216 far to the nozzle row 1. The angle θ3nN is an angle between the optical axis L and a direction from the n$^{th}$ nozzle 1n of the first nozzle row 1 to one end of the light receiving element 216 close to the nozzle row 1. The angle θ3nF is an angle between the optical axis L and a direction from the n$^{th}$ nozzle 1n of the first nozzle row 1 to the other end of the light receiving element 216 far to the nozzle row 1.

In the image forming device according to the first embodiment the ink droplet 202 is discharged from each nozzle (11, 12, ..., 1X, ..., 1n, 21, 22, ..., 2n, ..., M1, M2, ..., Mn) on the nozzle plane 201. The light beam 203 hits the ink droplet 202 and scatters as scattered light S.

The light receiving elements 206, 216 of the discharged liquid droplet detecting device 103 of the image forming device receive the scattered light S on the light receiving surfaces 207, 217 and convert it to a voltage. Thus, by measuring a converted output voltage V, the device 103 acquires data on the received scattered light S and detects, according to the data, a state of liquid droplets as the ink droplet 202 including presence or absence of the ink droplet 202 and straying of the ink droplet 202. Such a detected state is used for detected liquid droplet discharge data.

Next, the relationship between the intensity distribution of the light beam 203 and the light receiving elements 206, 216 when the angle between the optical axis L of the light beam 203 and nozzle row is zero and the optical axis L is not inclined (optical axis L0 in FIG. 2B) is described referring to FIG. 3. The upper graph of FIG. 3 shows the intensity distribution of the light beam 203 and abscissa axis represents Y-direction in FIGS. 2B, 2C and vertical axis represents optical intensity. The lower view shows the cross section of the light beam 203. As seen from the drawing, the intensity of the light beam 203 varies depending on the position in Y-direction and the intensity is highest at the optical axis L (L0) and decreases as the position approaches the end of the beam diameter in Y-direction. A part of ambient light of the light beam 203 indicated by hatching is offset light incident on the light receiving element 206 or 216 as described later. The intensity distribution of FIG. 3 is merely one example and changes depending on a condition including properties and positions of the light emitting element 204, collimator lens 205, and an aperture, and a distance from the light emitting element or collimator lens 205 to the ink droplet 202 (distance in Z-direction in FIG. 2A and else).

Figure 4:
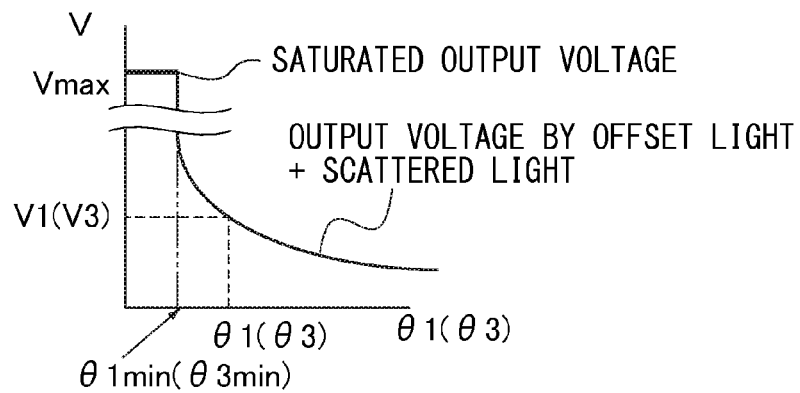
FIG. 4 is a graph showing a relationship between an angle $\theta_1$ ($\theta_3$) made by the light receiving elements and the optical axis of the light beam and an output voltage of the light receiving elements, when the tilt of the optical axis is zero.

FIG. 4 shows the relationship between the output voltage V of the light receiving element 206 or 216 and the angle θ1 or θ3 between the optical axis L (L0) of the light beam 203 and the direction from the position of the ink droplet 202 injected from the nozzle to the light receiving element 206 or 216. In FIG. 4 abscissa axis indicates the angle θ1 or θ3 and vertical axis indicates the output voltage V (V1 or V3) by offset light and scattered light.

As seen from FIG. 4, the output voltage V by the scattered light S shows angular dependency such that the larger the angle θ1 or θ3 is or the smaller the distance between the nozzle and light receiver B is, the smaller the output voltage V is. However, at angle θ1 min or θ3 min, the output voltage V reaches a saturation limit value Vmax even when the ink droplet 202 is not discharged for the reason (1) or (2) below, so that the scattered light S cannot be detected. Herein, the angle θ1 min or θ3 min is a minimal angle made by the light receiving element 206 or 216 and the optical axis L when the following conditions are not satisfied.
(1) When the light receiving element 206 or 216 is in the beam diameter φ2 of the light beam 203.
(2) When the light receiving element 206 or 216 is positioned such that the output thereof reaches or exceeds the saturation limit value of the offset light.

The offset light includes ambient light of the light beam 203 outside the beam diameter φ2 and noise light such as reflected light by the recording medium W, the inkjet head 100, and the other periphery elements. The offset light is incident on the light receiving elements 206 and 216. With an increase in the offset light amount, the output voltage V of the light receiving element 206 or 216 reaches the saturation limit value Vmax (saturated output voltage in FIG. 4) even when the ink droplet 202 is not discharged. This makes it impossible to detect scattered light S. The value of the offset light causing the saturated output voltage is defined to be offset light saturation value. Because of this, the angle θ1 or θ3 between the light receiving element 206 or 216 and the optical axis L needs to be θ1>θ1 min (θ3>θ3 min) which does not correspond to the conditions (1) and (2).

In FIG. 4 the output voltage V is a downward slope relative to the angle θ1 (θ3), but it can be a waveform downward slope depending on the shape and size of the ink droplet 202. At angle 0 (no tilt) between the optical axis L of the light beam 203 and the nozzle row, the light receiving elements 206, 216 are in the same distance from the optical axis L (L0 in FIG. 2B) so that they receive the same amount of offset light (for example, a part of the ambient light of the light beam 203 hatched in FIG. 3).

Figure 5A:
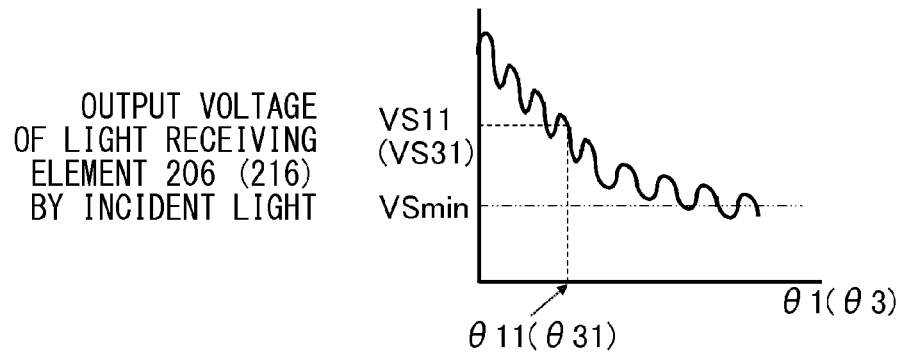
FIG. 5A is a graph showing a relationship between the angle $\theta_1$ ($\theta_3$) with no tilt of the optical axis and the amount of scattered light from ink droplets incident on the light receiving elements when the optical axis of the light beam is aligned with an ink droplet discharged from a first nozzle of a first row.
Figure 5B:
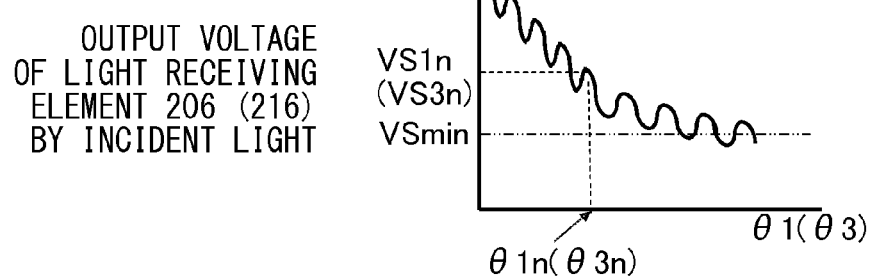
FIG. 5B shows the same when the optical axis is aligned with an ink droplet discharged from an $n^{th}$ nozzle of a first row.

Next, the relationship between the angle θ1 (θ3) and the scattered light amount from the ink droplet 202 incident on the light receiving element 206 or 216 is described referring to FIGS. 5A, 5B. In FIG. 5A the optical axis L0 of the light beam 203 is aligned with the first nozzle 11 of the first row while in FIG. 5B the optical axis L0 is aligned with the nozzle 1n of the first row.

The scattered light S from the ink droplet 202 is a waveform distribution having an angular dependency, as described above. The scattered light S changes in attenuation rate of waveform and height and width of amplitude in accordance with the components and shape of the ink droplet 202. If the wavelength of light incident on the ink droplet 202 and the components of the ink droplet 202 are unchanged and the size and shape of the ink droplet are almost the same, the scattered light amount varies depending on scattering angle and the larger the scattering angle or the closer the distance between the nozzle and the light receiver B, the more attenuated the scattered light amount. When the output voltage V by the scattered light S incident on the light receiving element 206, 216 decreases to the detectable threshold VSmin or less, scattered light S from the ink droplet 202 is undetectable.

With the optical axis L aligned on the ink droplet 202 from the first nozzle 11 of the first row far from the light receiver B, the incidence angle of the scattered light S on the light receiving element 206 or 216 is θ11 (θ31) in FIG. 5A. VS11 (VS31) is the output voltage by the scattered light S incident on the light receiving element 206 or 216 when the incidence angle θ11 (θ31) is within a range of θ11N to θ31F (θ31N to θ31F). The output voltage VS11 (VS31) is or exceeds the threshold VSmin so that the scattered light S from the ink droplet 202 is detectable.

Meanwhile, in FIG. 5B with the optical axis L aligned on the ink droplet 202 discharged from the n$^{th}$ nozzle 1n of the first row close to the light receiver B, the incidence angle of the scattered light S on the light receiving element 206 or 216 is $\theta 1n$ ($\theta 3n$). VS1$n$ (VS3$n$) is the output voltage by the scattered light S incident on the light receiving element 206 or 216 when the incidence angle $\theta 11$ ($\theta 31$) is within a range of the $\theta 1n$N to $\theta 1n$F ($\theta 3n$N to $\theta 3n$F). The output voltage VS1$n$ (VS3$n$) is or exceeds the threshold VSmin so that the scattered light S from the ink droplet 202 is detectable.

As described above, at the tilt 0 of the optical axis L (L0) relative to the nozzle row, the light receiving elements 206 and 216 are in the same distance from the optical axis L0 and the angles $\theta 1$ and $\theta 3$ are at the same position or line-symmetric. When the optical axis L of the light beam 203 is adjusted to be on the ink droplet 202 discharged from the nozzle 11 or 1$n$ as shown in FIGS. 4, 5A and 5B, the offset light received by both of the light receiving elements 206, 216 is less than the saturation limit value and their output voltages are or exceed the threshold VSmin of the scattered light amount. Thus, either of the light receiving elements 206, 216 can be selected. There may be individual variability in the detected values of the light receiving elements 206, 216 due to usage environment or a deviation in the offset light. It is preferable to select one of the light receiving elements 206, 216 less affected by the offset light.

Figure 6A:
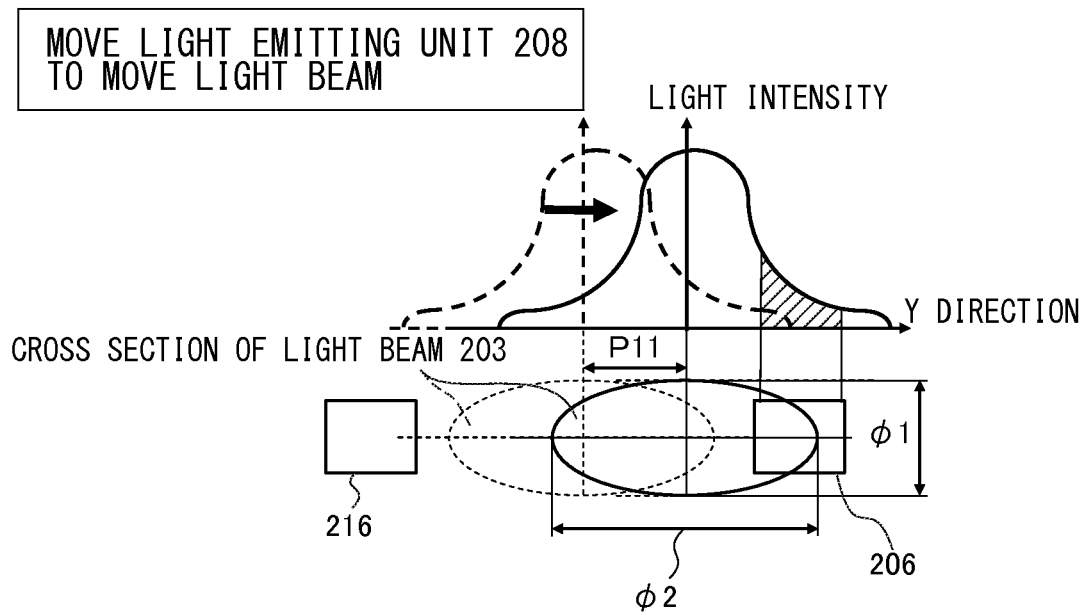
FIG. 6A shows a relationship between the intensity distribution of the light beam and each light receiving element with the tilt $\theta_{20}$ of the optical axis when the optical axis of the light beam is aligned with an ink droplet discharged from a first nozzle of a first row.
Figure 6B:
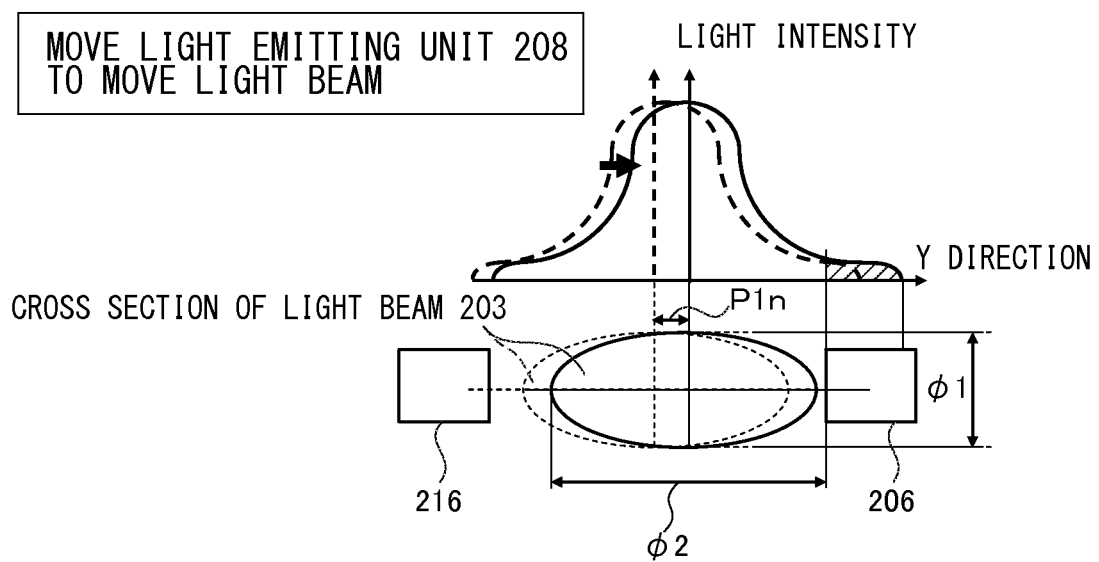
FIG. 6B shows the same when the optical axis is aligned with an ink droplet discharged from an $n^{th}$ nozzle of a first row.

Next, a description is made on a case where the optical axis L is tilted at angle $\theta 20$ toward the light receiving element 206, referring to FIGS. 6A, 6B. With such a tilt of the optical axis L, the light receiving element 206 is closer or in a smaller distance to the light beam 203 while the light receiving element 216 is further or in a larger distance from the light beam 203 than with no tilt of the optical axis L. Thereby, the angle $\theta 3$ becomes larger than the angle $\theta 1$. FIGS. 6A, 6B show a relationship between the intensity distribution of the light beam 203 and the light receiving elements 206, 216 when the optical axis L of the light beam 203 is tilted at angle $\theta 20$ toward the light receiving element 206. FIG. 6A shows the relationship when the optical axis L of the light beam is on the ink droplet 202 from the first nozzle 11 of the first row and FIG. 6B shows the same when the optical axis is on the ink droplet 202 from the $n^{th}$ nozzle 1$n$ of the first row. The upper views of FIGS. 6A, 6B show the intensity distribution of the light beam 203 and abscissa axis represents Y-direction in FIGS. 2B, 2C and vertical axis represents optical intensity. The lower views show the cross section of the light beam 203. A part of ambient light of the light beam 203 indicated by hatching is incident on the light receiving element 206 or 216 as the offset light. The intensity distribution of FIGS. 6A, 6B is merely one example and changes depending on a condition including properties and positions of the light emitting element 204, collimator lens 205, and an aperture, and distance from the light emitting element or collimator lens 205 to the ink droplet 202 (distance in Z-direction in FIG. 2A and else).

In this case the moving unit 210 moves the light emitting unit 208 to be able to adjust the optical axis L of the light beam 203 to be on the ink droplet 202 discharged from the nozzle 11 or 11$n$. The reference codes P11, P1$n$ in FIG. 6A, 6B represent offset amounts P between the optical axis L and the non-tilted optical axis L0 when the optical axis L is on the nozzle 11 and nozzle 1$n$ in FIGS. 2B, 2C respectively.

Figure 7A:
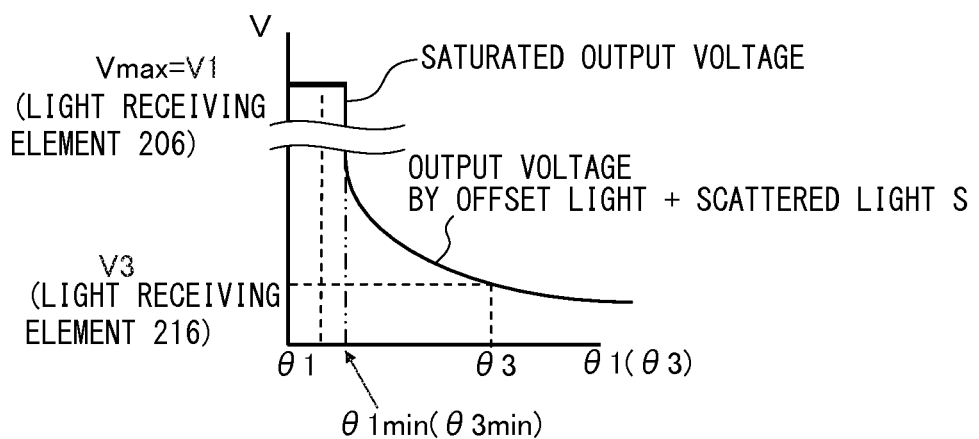
FIG. 7A is a graph showing a relationship between the angle $\theta 1$ ($\theta 3$) and the output voltage of the light receiving elements with the tilt $\theta 20$ of the optical axis when the optical axis of the light beam is aligned with an ink droplet discharged from a first nozzle of a first row.
Figure 7B:
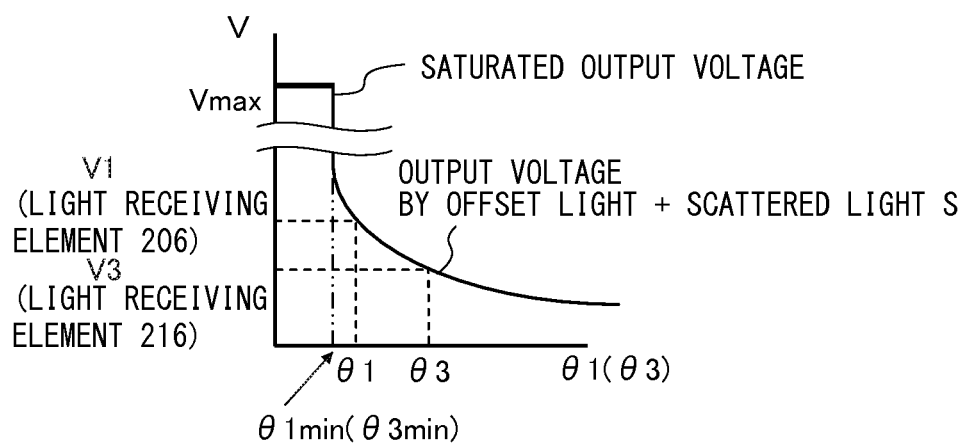
FIG. 7B shows the same when the optical axis is aligned with an ink droplet discharged from an $n^{th}$ nozzle of a first row.

FIGS. 7A, 7B show a relationship between the angle $\theta 1$ ($\theta 3$) between the light receiving elements 206, 216 and the optical axis L of the light beam 203 and the output voltage V1 (V3) of the light receiving elements 206, 216 by the offset light and scattered light when the optical axis is tilted at $\theta 20$ toward the light receiving element 206. FIG. 7A shows the relationship when the optical axis L of the light beam 203 is on the ink droplet 202 from the first nozzle 11 of the first row in FIG. 2B, and FIG. 7B shows the relationship when the optical axis L is on the ink droplet 202 from the $n^{th}$ nozzle 1$n$ of the first row in FIG. 2C.

In FIG. 7A with the optical axis L on the ink droplet 202 from the nozzle 11 further from the light receiver B, the angle $\theta 1$ of the light receiving element 206 closer to the light beam 203 is smaller than $\theta 1$ min. Because of this, the output voltage V1 of the light receiving element 206 reaches the saturation limit value Vmax of the offset light so that the scattered light cannot be detected. Further, the angle $\theta 3$ of the light receiving element 216 further from the light beam 203 is larger than $\theta 3$ min. The output voltage V3 of the light receiving element 216 is the saturation limit value Vmax or less so that the scattered light S from the ink droplet 202 can be detected.

Meanwhile, in FIG. 7B with the optical axis L on the ink droplet 202 from the nozzle 1$n$ closer to the light receiver B, the angle $\theta 1$ of the light receiving element 206 closer to the light beam 203 is larger than $\theta 1$ min. Because of this, the output voltage V1 of the light receiving element 206 is equal to or smaller than the saturation limit value Vmax of the offset light so that the scattered light can be detected. Further, the angle $\theta 3$ of the light receiving element 216 further from the light beam 203 is larger than $\theta 3$ min. The output voltage V3 of the light receiving element 216 is the saturation limit value Vmax or less so that the scattered light S from the ink droplet 202 can be detected.

Similarly to FIG. 4, the output voltages V1, V3 in FIGS. 7A, 7B are downward slopes relative to the angles $\theta 1$ and $\theta 3$, but they can be downward waveform slopes depending on the shape and size of the ink droplet 202. At tilt angle $\theta 20$ of the optical axis L, the light receiving elements 206, 216 are in different distances from the optical axis L (L0 in FIG. 2B) so that the amounts of offset light they receive (for example, a part of the ambient light of the light beam 203 hatched in FIGS. 6A, 6B) are different.

Figure 8A:
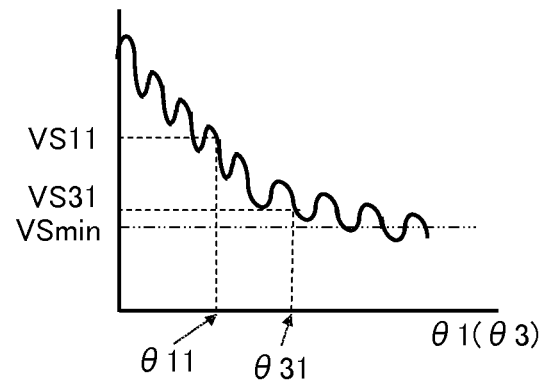
FIG. 8A is a graph showing a relationship between the angle $\theta 1$ ($\theta 3$) and the amount of the scattered light from ink droplets incident on the light receiving elements with the tilt $\theta 20$ of the optical axis when the optical axis of the light beam is aligned with an ink droplet discharged from a first nozzle of a first row.
Figure 8B:
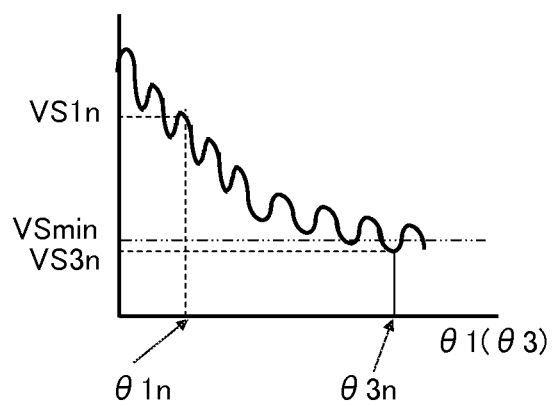
FIG. 8B shows the same when the optical axis is aligned with an ink droplet discharged from an $n^{th}$ nozzle of a first row.

Next, FIGS. 8A, 8B show a relationship between the angle $\theta 1$ ($\theta 3$) and the scattered light amount incident from the ink droplet 202 on the light receiving element 206 or 216 when the optical axis L is tilted at the tilt angle $\theta 20$ toward the light receiving element 206. FIG. 8A shows the relationship when the optical axis L of the light beam 203 is on the ink droplet 202 from the first nozzle 11 of the first row. FIG. 8B shows the relationship when the optical axis is on the ink droplet 202 from the $n^{th}$ nozzle 1$n$ of the first row.

In FIG. 8A with the optical axis L on the ink droplet 202 from the nozzle 11 further from the light receiver B, the incidence angle of the scattered light S on the light receiving element 206 or 216 is $\theta 11$ ($\theta 31$). VS11 (VS31) is the output voltage by the scattered light S incident on the light receiving element 206 or 216 when the incidence angle $\theta 11$ ($\theta 31$) is within a range of the $\theta 11$N to $\theta 31$F ($\theta 31$N to $\theta 31$F). The angle $\theta 1$ of the light receiving element 206 close to the light beam 203 is smaller and so is the incidence angle $\theta 11$ of the scattered light S. Thus, the output voltage VS11 by the scattered light S incident on the light receiving element 206 is or exceeds the threshold Vsmin so that the scattered light S from the ink droplet 202 is detectable. The angle $\theta 3$ of the light receiving element 216 further from the light beam 203 is larger and so is the incidence angle $\theta 31$ of the scattered light S. Thus, the output voltage VS 31 by the scattered light S incident on the light receiving element 216 is decreased but the scattered light amount is the threshold VSmin or more so that the scattered light S from the ink droplet 202 is detectable.

Meanwhile, in FIG. 8B with the optical axis L on the ink droplet 202 discharged from the $n^{th}$ nozzle 1$n$ of the first row closer to the light receiver B, the incidence angle of the scattered light S on the light receiving element 206 or 216 is $\theta1n$ ($\theta3n$). VS$1n$ (VS$3n$) is the output voltage by the scattered light S incident on the light receiving element 206 or 216 when the incidence angle $\theta1n$ ($\theta3n$) is within a range of $\theta1n$N to $\theta1n$F ($\theta3n$N to $\theta3n$F). The angle $\theta1$ of the light receiving element 206 closer to the light beam 203 is smaller and so is the incidence angle $\theta1n$ of the scattered light S. Thus, the output voltage VS11 by the scattered light S incident on the light receiving element 206 is or exceeds the threshold VSmin or more so that the scattered light S from the ink droplet 202 is detectable. The angle $\theta3$ of the light receiving element 216 further from the light beam 203 is larger and so is the incidence angle $\theta3n$ of the scattered light S. Thus, the output voltage VS31 by the scattered light S incident on the light receiving element 216 is smaller than the threshold VSmin so that the scattered light S from the ink droplet 202 is undetectable.

As described above, in FIGS. 7A, 8A when the optical axis L of the light beam 203 is adjusted to be on the ink droplet 202 discharged from the nozzle 11 further from the light receiver B, in the light receiving element 216 the offset light amount is the saturation limit value Vmax or less and the scattered light amount is threshold Vsmin or more. Therefore, the light receiving element 216 is selected to detect the scattered light S from the ink droplet 202. That is, for the first nozzle 11 of the first row further from the light receiver B and closer to the light emitter A, the light receiving element 216 further from the light beam 203 is the one to be selected. The offset light amount thereof does not exceed the saturation limit value and and the scattered light amount is the detectable threshold or more. Accordingly, it is able to precisely detect the scattered light S from the ink droplet 202 and determine a state of the discharged ink droplet 202 more accurately.

Meanwhile, in FIGS. 7B, 8B when the optical axis L of the light beam 203 is adjusted to be on the ink droplet 202 discharged from the nozzle $1n$ closer to the light receiver B, in the light receiving element 206 the offset light amount is the saturation limit value Vmax or less and the scattered light amount is the threshold Vsmin or more. Therefore, the light receiving element 206 is selected to detect the scattered light S from the ink droplet 202. That is, for the $n^{th}$ nozzle $1n$ of the first row closer to the light receiver B, the light receiving element 206 closer to the light beam 203 is the one to be selected. The offset light amount thereof does not exceed the saturation limit value and the scattered light amount from the ink droplet 202 is or exceeds the threshold. Accordingly, it is able to precisely detect the scattered light S from the ink droplet 202 and determine a state of discharged ink droplet 202 more accurately.

Thus, one of the light receiving elements 206, 216 are determined to receive the scattered light S from the ink droplet 202 on the basis of the distance between the nozzle as a subject of detection and the light receiver B and the distance between the light beam 203 and the light receiving elements 206, 216. For instance, for the first to $X-1^{th}$ nozzles 11 to 1(X-1) of the first row in a larger distance from the light receiver B than a certain value, the light receiving element 216 further from the light beam 203 is set to detect the scattered light from the ink droplet 202 since the offset light amount is the saturation limit value Vmax or less and the scattered light amount is the threshold VSmin more. Meanwhile, for the $X^{th}$ to $n^{th}$ nozzles 1X to $1n$ in a smaller distance from the light receiver B than the certain value, the light receiving element 206 closer to the light beam 203 is set to detect the scattered light from the ink droplet 202 since the offset light amount is the saturation limit value or less and the scattered light amount is the threshold VSmin more. The value of X, that is, the distance from the light receiver B to the nozzle X, changes depending on the wavelength of light incident on the ink droplet 202, the components, shape and size of the ink droplet 202, the distance from the light emitting element 204 to the nozzle, the nozzle interval, the distance between the nozzle and the light receiving element 206, the positional relation between the light beam and the light receiving element 206, and the angles $\theta20$, $\theta1$, $\theta2$, $\theta4$, $\theta3$. The certain value specifically refers to a distance between the position of the ink droplet 202 discharged from the nozzle in question and the light receiving element 216 when the output voltage of the light receiving element 216 further from the light beam 203 exceeds the saturation limit value Vmax or is less than the threshold VSmin. The light receiving element 216 detects a state of liquid droplets discharged from the $1^{st}$ to $X-1^{th}$ nozzles in a distance of the certain value and the light receiving element 206 conducts the detection for the $X^{th}$ and subsequent nozzles.

Moreover, M+1 light receiving elements are provided outside the nozzle row 1 (opposite to the nozzle row 2), between the nozzle rows 1 and 2, nozzle rows 2 and 3, . . . , nozzle row X-1 and nozzle row X, nozzle row X and nozzle row X+1, . . . , and nozzle rows M-1 and M, and outside the nozzle row M (opposite to the nozzle row M-1). Thereby, a pair of light receiving elements is disposed on both sides from each nozzle row, making it possible to select either of the pair for detection in accordance with various conditions and accurately detect the scattered light S from the ink droplets 202 of each nozzle row. Moreover, a single light receiving element can conduct the detection for the two nozzle rows on both sides thereof at low costs, with the angles $\theta2$ and $\theta4$ of the light receiving element relative to the vertical direction of the optical axis L set to 0. Furthermore, the angles $\theta2$ and $\theta4$ can be changed in line with a nozzle row to be detected by use of an arbitrary driver. This can further improve the accuracy at which the light receiving element detects liquid droplets from each nozzle row.

Further, when every two nozzle rows 1 and 2, 3 and 4 . . . , X-1 and X, . . . , M-1 and M are adjacent to each other, two light receiving elements are used for every two nozzle rows. That is, M/2+1 light receiving elements are provided outside the nozzle row 1 (opposite to the nozzle row 2), between the nozzle rows 1 and 2, nozzle rows 2 and 3, . . . , nozzle row X-2 and nozzle row X-1, nozzle row X+1 and nozzle row X+2, . . . , and nozzle rows M-2 and M-1, and outside the nozzle row M (opposite to the nozzle row M—1). In this manner a pair of light receiving elements are also disposed on both sides of each nozzle row, making it possible to select either of the pair for detection in accordance with various conditions and accurately detect the scattered light S from the ink droplets 202 from each nozzle row. Further, a reduction in the number of light receiving elements leads to reducing the manufacturing costs of the device. Alternatively, cost reduction is attainable by setting the angles $\theta2$ and $\theta4$ to 0 or the accuracy of detection can be improved by properly changing the angles $\theta2$ and $\theta4$ in accordance with a nozzle row to be detected.

As described above, the discharged liquid droplet detecting device according to the first embodiment comprises the pair of light receiving elements placed on both sides of the beam diameter of the light beam from the light emitter. Because of this, even with a nozzle displaced from the arranged nozzle rows or a tilted light beam due to a tilt of the light emitting element or a lens, either of the pair can accurately detect a state of discharged ink droplets. Moreover, the image forming device incorporating such a discharged liquid droplet detecting device can properly reduce operation stops and prevent degradation of image quality.

Figure 9:
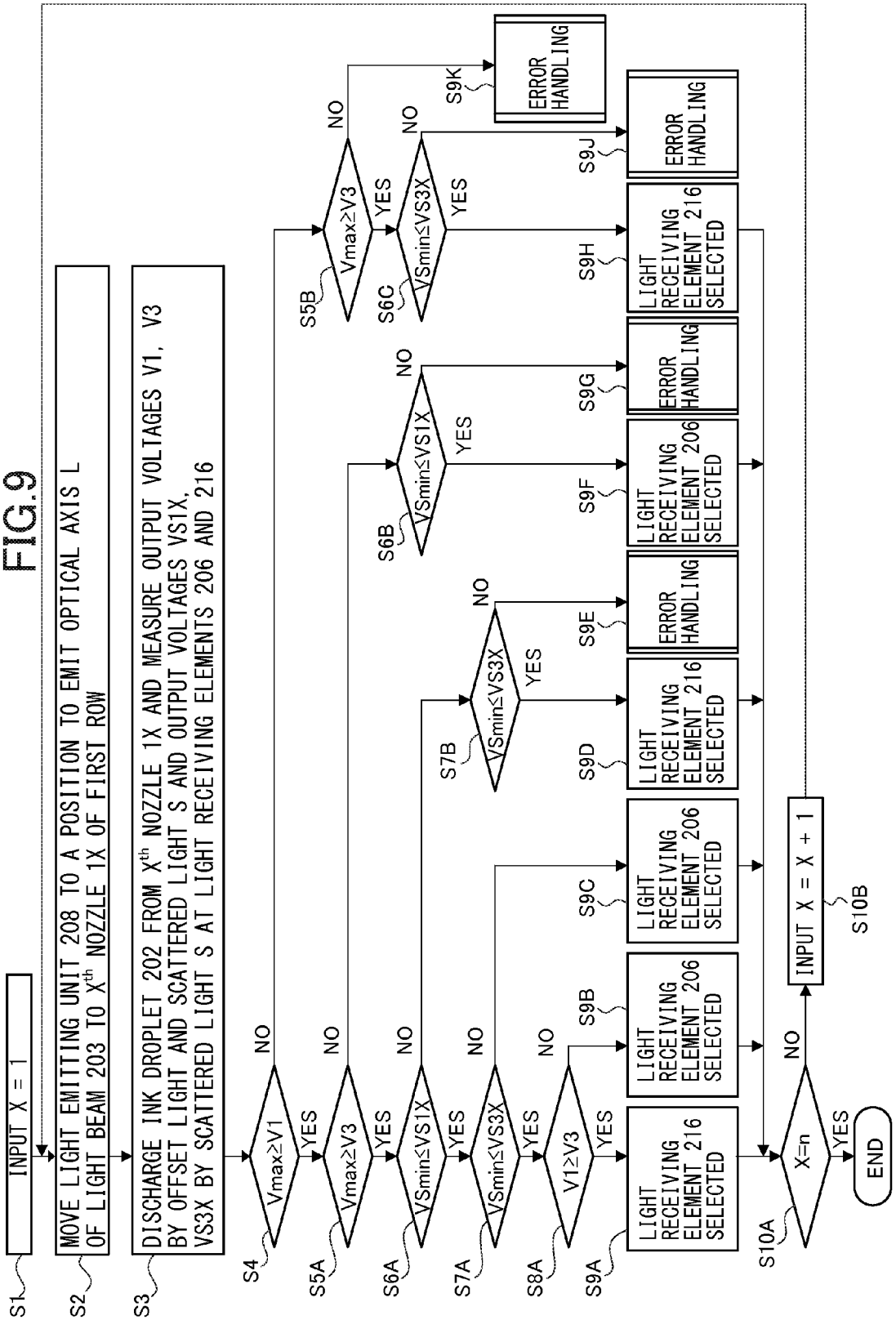
FIG. 9 is a flowchart of how to select a light receiving element in the discharged liquid droplet detecting device according to the first embodiment.

Next, the procedure of selecting the light receiving element is described in detail, referring to FIG. 9. In FIG. 9 and following figures, either of the light receiving elements 206, 216 of the discharged liquid droplet detecting device 103 is selected for the first to $n^{th}$ nozzles 11 to 1n of the first row by way of example.

In step S1 X is assigned 1 to detect a state of the ink droplet 202 from the first nozzle 11 of the first row. In step S2 the moving unit 210 is moved to move the light emitting unit 208 to emit the optical axis L of the light beam 203 to the ink droplet 202 discharged from an $X^{th}$ nozzle 1X (nozzle 11 at first) of the first row.

In step S3 the light receiving elements 206 and 216 receive the scattered light S at timing at which the ink droplet 202 is discharged from the nozzle 1X and obtain a measured value. On the basis of the measured value, the output voltages V1, V3 by the offset light and scattered light S and the output voltages VS1X, VS3X by the scattered light S are calculated. The output voltages VS1X, VS3X are acquired by subtracting a pre-measured output value by the offset light from the output voltages V1, V3. Specifically, the current values from the light receiving elements 206, 216 are converted to voltages by a current-voltage converter and amplified at an arbitrary multiplying factor n to extract the output voltages V1, V3 by the offset light and scattered light S. Also, the output voltages VS1X, VS3X can be extracted by removing the offset light as DC components from the output voltages V1, V3 by AC coupling, for example. The output voltages VS1X, VS3X are amplified at an arbitrary multiplying factor m. In step S4 a magnitude relation between the output voltage V1 of the element 206 by the offset light and scattered light S and a saturated output voltage (saturation limit value) Vmax thereof is determined. At Vmax≥V1 (Yes in step S4), the flow proceeds to step S5A. At Vmax<V1 (No in step S4), the light receiving element 206 is not able to detect the scattered light S and the flow proceeds to step S5B.

In step S5A a magnitude relation between the output voltage V3 of the element 216 by the offset light and scattered light S and a saturated output voltage (saturation limit value) Vmax thereof is determined. At Vmax≥V3 (Yes in step S5A), the flow proceeds to step S6A. At Vmax<V3 (No in step S5A), the light receiving element 216 is not able to detect the scattered light S and the flow proceeds to step S6B.

In step S5B a magnitude relation between the output voltage V3 of the element 216 by the offset light and scattered light S and a saturated output voltage (saturation limit value) Vmax thereof is determined. At Vmax≥V3 (Yes in step S5B), the flow proceeds to step S6C. At Vmax<V3 (No in step S5B), both the light receiving elements 206, 216 are not able to detect the scattered light S and the flow proceeds to step S9K.

In step S6A a magnitude relation between the output voltage VS1X of the element 206 by the scattered light S and the threshold VSmin of the scattered light is determined. At VSmin≤VS1X (Yes in step S6A), the light receiving element 206 is able to detect the scattered light S and the flow proceeds to step S7A. At VSmin>VS1X (No in step S6A), the light receiving element 216 is not able to detect the scattered light S and the flow proceeds to step S7B.

In step S6B a magnitude relation between the output voltage VS1X of the element 206 by the scattered light S and the threshold VSmin of the scattered light is determined. At VSmin≤VS1X (Yes in step S6B), the light receiving element 206 is able to detect the scattered light S and the flow proceeds to step S9F to select the light receiving element 206. At VSmin>VS1X (No in step S6B), both the light receiving elements 206, 216 are not able to detect the scattered light S and the flow proceeds to step S9G for error handling.

In step S6C a magnitude relation between the output voltage VS3X of the element 216 by the scattered light S and the threshold VSmin thereof is determined. At VSmin VS3X (Yes in step S6C), the light receiving element 206 is able to detect the scattered light S and the flow proceeds to step S9H. At VSmin>VS3X (No in step S6C), both the light receiving elements 206, 216 are not able to detect the scattered light S and the flow proceeds to step S9J for error handling.

In step S7A a magnitude relation between the output voltage VS3X of the element 216 by the scattered light S and the threshold VSmin of the scattered light is determined. At VSmin≤VS3X (Yes in step S7A), the light receiving element 206 is able to detect the scattered light S and the flow proceeds to step S8A. At VSmin>VS3X (No in step S7A), the light receiving element 206 is able to detect the scattered light S and the flow proceeds to step S9C to select the light receiving element 206.

In step S7B a magnitude relation between the output voltage VS3X of the element 216 by the scattered light S and the threshold VSmin of the scattered light is determined. At VSmin≤VS3X (Yes in step S7B), the light receiving element 216 is able to detect the scattered light S and the flow proceeds to step S9D to select the light receiving element 216. At VSmin>VS3X (No in step S7B), both the light receiving elements 206, 216 are not able to detect the scattered light S and the flow proceeds to step S9E for error handling.

In step S8A a magnitude relation between the output voltage V1 of the element 206 by the offset light and scattered light S and the output voltage V3 of the element 216 by the offset light and scattered light is determined. At V1≥V3 (Yes in step S8A), the light receiving element 216 has a larger margin (less affected by the offset light) and the flow proceeds to step S9A to select the light receiving element 216. At V1<V3 (No in step S8A), the light receiving element 206 has a larger margin and the flow proceeds to step S9B to select the light receiving element 206.

In steps S9A, S9D, and S9H the light receiving element 216 is determined to be the one to detect a state of liquid droplets, and the flow proceeds to step S10A. In steps S9B, S9C, and S9F the light receiving element 206 is determined to be the one to detect a state of liquid droplets, and the flow proceeds to step S10A. In steps S9E, S9G, S9J, and S9K both of the light receiving elements 206, 216 are not able to detect so that error handling is conducted, and the flow proceeds to step S10A. Error handling is for example sending an error notice to the image forming device. Receiving an error notice, the image forming device deals with an error in accordance with a user's setting by the following operations (1) to (4), to prevent a degradation of image quality.

(1) Stops operating, displays an error message, and waits for a user's instruction.
(2) Executes head-cleaning.
(3) Executes discharged liquid droplet detection again after head-cleaning.
(4) Executes test printing after executing head-cleaning and discharged liquid droplet detection again.

In step S10A a determination is made on whether or not the $X^{th}$ nozzle is an $n^{th}$ nozzle. At X=n (Yes in step S10A), the detecting light receiving elements have been determined for all the nozzles and the flow is completed. At X being not n (No in step S10A), the flow proceeds to step S10B, setting a different nozzle as a subject of detection.

In step S10B X is counted up to X+1 to select either of the light receiving elements for the nozzle in question, and the flow returns to step S2 and executes the step S2 and following steps.

FIG. 9 shows a flow of selecting a light receiving element, however, it is possible to detect discharged ink droplets concurrently with selecting a light receiving element.

Second Embodiment

Figure 10A:
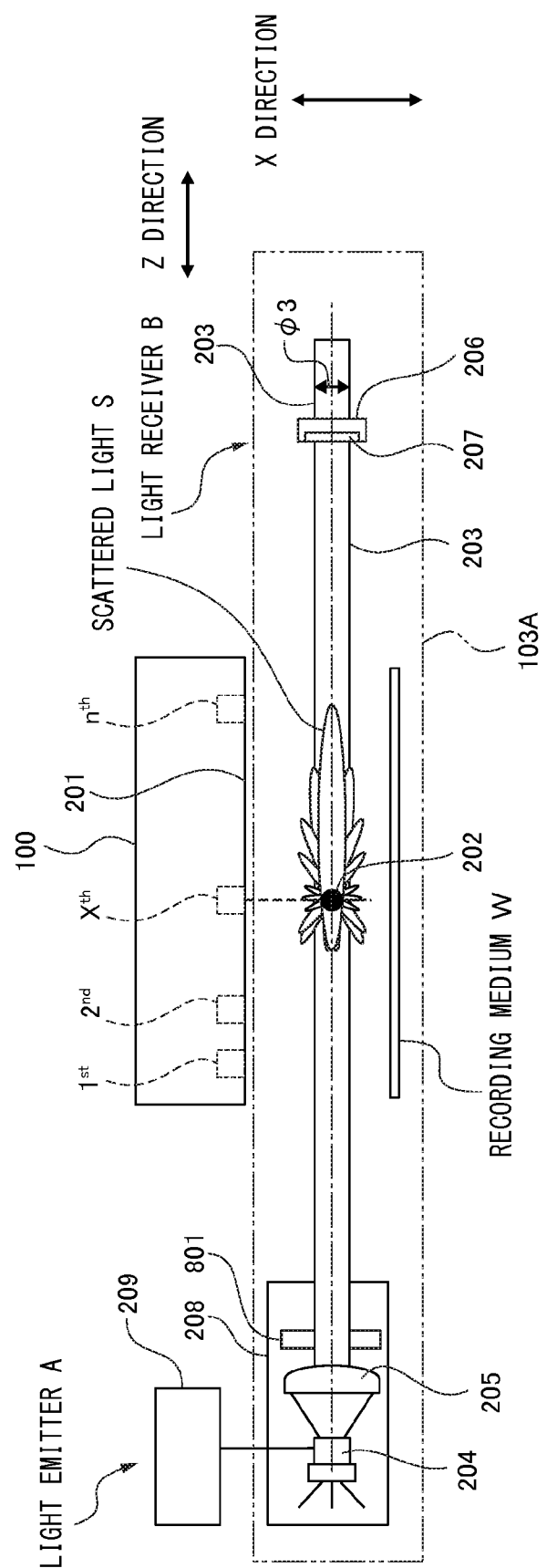
FIG. 10A is a schematic side view of an inkjet head and a discharged liquid droplet detecting device according to a second embodiment by way of example.
Figure 10D:
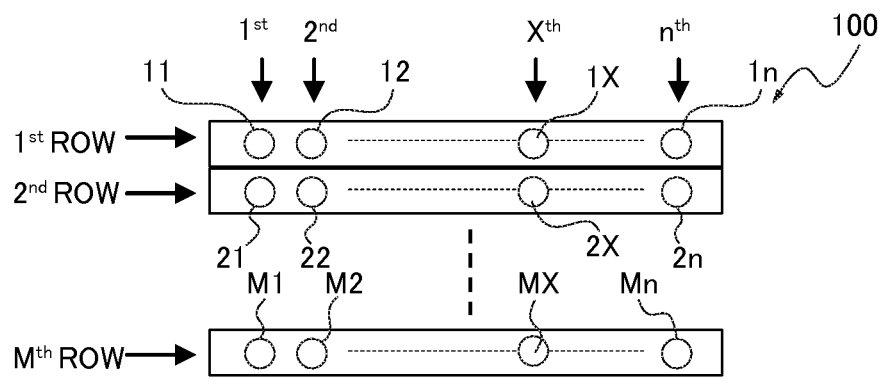
FIG. 10D is a schematic overhead semi-cross section view of the inkjet head of the discharged liquid droplet detecting device according to the second embodiment by way of example.

Now, the structure of a discharged liquid droplet detecting device according to a second embodiment is described with reference to FIG. 10A to FIG. 10D. FIG. 10A is a schematic side view of an inkjet head 100 and a discharged liquid droplet detecting device 103A according to the second embodiment. FIG. 10B is a schematic overhead view of the discharged liquid droplet detecting device 103A when the optical axis L of the light beam 203 is on the first nozzle 11 of the first row. FIG. 10C is a schematic overhead view of the discharged liquid droplet detecting device 103A when the optical axis L of the light beam 203 is on the $n^{th}$ nozzle $1n$ of the first row. FIG. 10D is a schematic overhead semi-cross section view of the inkjet head 100.

As shown in FIG. 10A to FIG. 10D, the discharged liquid droplet detecting device 103A has the same basic structure as the device 103 in the first embodiment and additionally comprises an aperture 801. The same or like parts and elements are given the same reference codes and a description thereof is omitted. In the second embodiment the aperture 801 is provided more downstream than the collimator lens 205 in the traveling direction of the light beam 203, to narrow down the light beam 203 from the light emitting element 204. The light emitting element 204, collimator lens 205, and aperture 801 are incorporated in the light emitting unit 208. The aperture 801 can be a known member such as an aperture or a slit, but it should not be limited thereto.

The light beam 203 from the light emitting element 204 of the light emitter A is converted to a parallel beam in beam diameters $\phi 3$ and $\phi 4$. Herein, $\phi 3$ and $\phi 4$ represent major and minor beam diameters, respectively. Either of the beam diameters $\phi 3$, $\phi 4$ can be set to the major axis, both of them can be the same ($\phi 3 = \phi 4$), or the shape of the beam can be rectangular or not depending on various kinds of conditions. Such conditions include the wavelength and intensity distribution of the light beam 203, the interval between the nozzle rows, the shape and size of the ink droplet 202, the type and radiation angle of the light emitting element 204, the distance between the light emitting element 204 and the collimator lens 205, the distance between the light emitting element 204 and the ink droplet 202, the distance between the ink droplet 202 and the light receiving elements 206, 216, the position and size of the light receiving elements 206, 216, and the distance between the inkjet head 100 and a printing material (recording medium W).

The two light receiving elements 206, 216 of the light receiver B are disposed outside the beam diameter $\phi 4$ of the light beam 203 so that their light receiving surfaces 207, 217 do not enter the beam diameter $\phi 4$ and their output voltages are not to exceed a saturation limit value of offset light. However, it is preferable to place the light receiving elements 206, 216 adjacent to the beam diameter $\phi 4$ at symmetric positions relative to the optical axis L of the light beam 203, that is, in equal distances from the optical axis L.

Further, the light receiving element 206 is disposed at angle $\theta 5$ relative to the optical axis L and at angle $\theta 6$ ($0 \leq \theta 6 < \theta 5$) relative to the vertical direction of the optical axis L. The angles $\theta 5$ and $6$ correspond to the angles $\theta 1$ and $\theta 2$ in the first embodiment. The light receiving element 216 is disposed at angle $\theta 7$ relative to the optical axis L and at angle $\theta 8$ ($0 \leq \theta 8 < \theta 7$) relative to the vertical direction of the optical axis L. The angles $\theta 7$ and $8$ correspond to the angles $\theta 3$ and $\theta 4$ in the first embodiment.

The angles $\theta 5$ and $\theta 7$ have to be in a range of $\theta 5 > \theta 5$ min and $\theta 7 > \theta 7$ min, respectively, which do not correspond to the above-mentioned conditions (1) and (2). The angles $\theta 5$ min and $\theta 7$ min are minimal angles between the light receiving elements 206 and 216 and the optical axis L, respectively.

The angle $\theta 5$ is represented as $\theta 51N$, $\theta 51F$, $\theta 5nN$, $\theta 5nF$ and the angle $\theta 7$ is represented as $\theta 71nN$, $\theta 71nF$, $\theta 7nN$, $\theta 7nF$ in FIGS. 10B, 10C. The angles $\theta 51N$ and $\theta 71N$ in FIG. 10B are angles between the optical axis L and a direction from the first nozzle 11 of the first row 1 to one ends of the light receiving elements 206, 216 close to the first row 1. The angles $\theta 51F$ and $\theta 71F$ are angles between the optical axis L and a direction from the first nozzle 11 of the first row 1 to the other ends of the light receiving elements 206 and 216 far to the first row. The angles $\theta 5nN$ and $\theta 7nN$ in FIG. 10C are angles between the optical axis L and a direction from the $n^{th}$ nozzle $1n$ of the first row 1 to one ends of the light receiving elements 206 and 216 close to the first row 1. The angles $\theta 5nF$ and $\theta 7nF$ are angles between the optical axis L and a direction from the first nozzle 11 of the first row 1 to the other ends of the light receiving elements 206 and 216 far to the nozzle row 1.

According to the second embodiment the additionally provided aperture 801 can reduce the beam diameters $\phi 3$, $\phi 4$ of the light beam 203. The beam diameters $\phi 3$, $\phi 4$ are smaller than those $\phi 1$, $\phi 2$ in the first embodiment ($\phi 4 < \phi 2$, ($\phi 3 < \phi 1$). As a result, the angles $\theta 5$, $\theta 7$ between the optical axis L and light receiving elements 206, 216 can be made smaller than the angles $\theta 1$, $\theta 3$.

Figure 11:
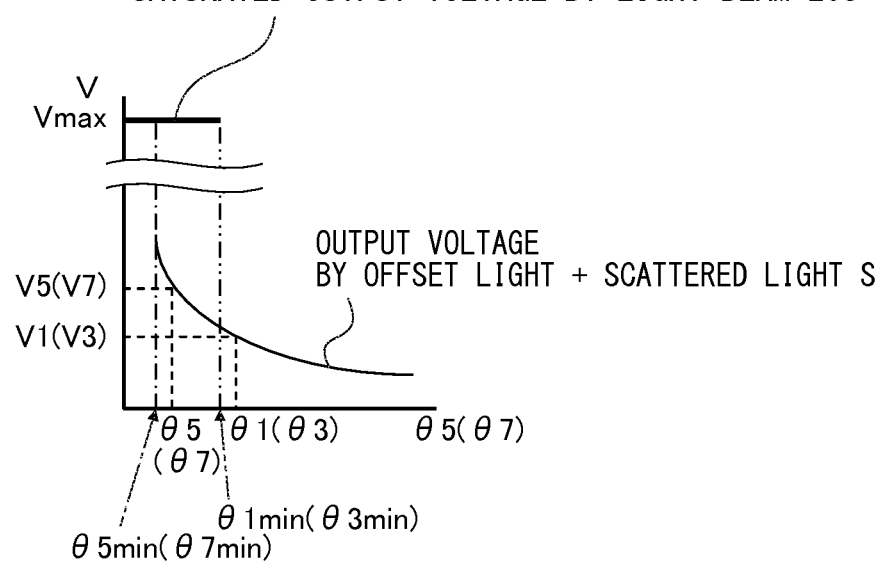
FIG. 11 is a graph showing a relationship between the angle $\theta 5$ ($\theta 7$) made by the light receiving elements and the optical axis of the light beam and the output voltage of the light receiving elements.

Next, the relationship between the output voltage V of the light receiving element 206 or 216 and the angle $\theta 5$ ($\theta 7$) between the light receiving element 206 or 216 and the optical axis L of the light beam 203 in the second embodiment is described, referring to FIG. 11. In FIG. 11 abscissa axis indicates the angles $\theta 5$ ($\theta 7$) and vertical axis indicates the output voltage V5 (V7) by the scattered light S.

As seen from FIG. 11, the output voltage V by the scattered light S shows angular dependency such that the larger the angle $\theta 5$ or $\theta 7$ is, the smaller the output voltage V is. Accordingly, under the condition of the angle $\theta 5 < \theta 1$ ($\theta 7 < \theta 3$), the amount of the received scattered light S is increased. The light-voltage converted output voltage V5 (V7) of the light receiving element 206 (216) at the angle $\theta 5$ ($\theta 7$) are larger than the output voltages V1 (V3) at the angle $\theta 1$ ($\theta 3$) (V1<V5, V3<V7) in the first embodiment.

As in the first embodiment, the discharged liquid droplet detecting device 103A can accurately detect a state of discharged ink droplets. The image forming device incorporating this discharged liquid droplet detecting device 103A can prevent degradation of image quality properly. Further, in the second embodiment the beam diameters of the light beam 203 are narrowed so that the angles $\theta 5$, $\theta 7$ of the light receiving elements 206, 216 can be decreased. This can increase the amount of the scattered light S from the discharged ink droplet 202 received by the light receiving elements 206, 216 relative to the amount of noise light N (offset light) including reflected light of the light beam 203 by the recording medium W and inkjet head 100 and ambient light. As a result, S/N ratio is enlarged, improving the accuracy at which the scattered light S is detected and resulting in more reliably detecting the state of discharged ink droplets 202.

Furthermore, according to the second embodiment the aberrations of the light emitting element 204 and collimator lens 205 can be reduced by narrowing the light beam 203 from the light emitting element 204, to suppress a variation in the light intensity and wavefront aberration of the light beam 203. Accordingly, it is also able to suppress a variation in the light intensity and wavefront aberration of the scattered light S occurring from the light beam 203's hitting the ink droplet 202, resulting in improving the accuracy at which the state of discharged ink droplets 202 is detected.

Third Embodiment

Figure 12A:
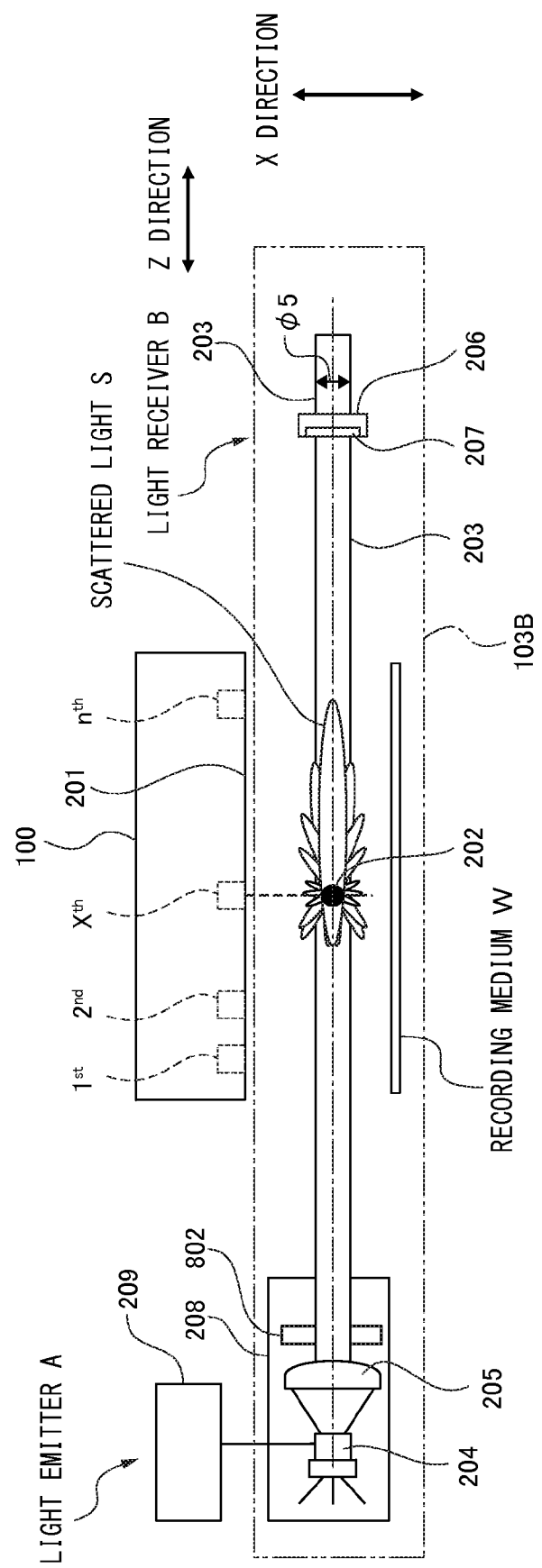
FIG. 12A is a schematic side view of an inkjet head and a discharged liquid droplet detecting device according to a third embodiment by way of example.

Next, the structure of a discharged liquid droplet detecting device according to a third embodiment is described with reference to FIG. 12A to FIG. 12D. FIG. 12A is a schematic side view of an inkjet head 100 and a discharged liquid droplet detecting device 103B according to the third embodiment.

Figure 12B:
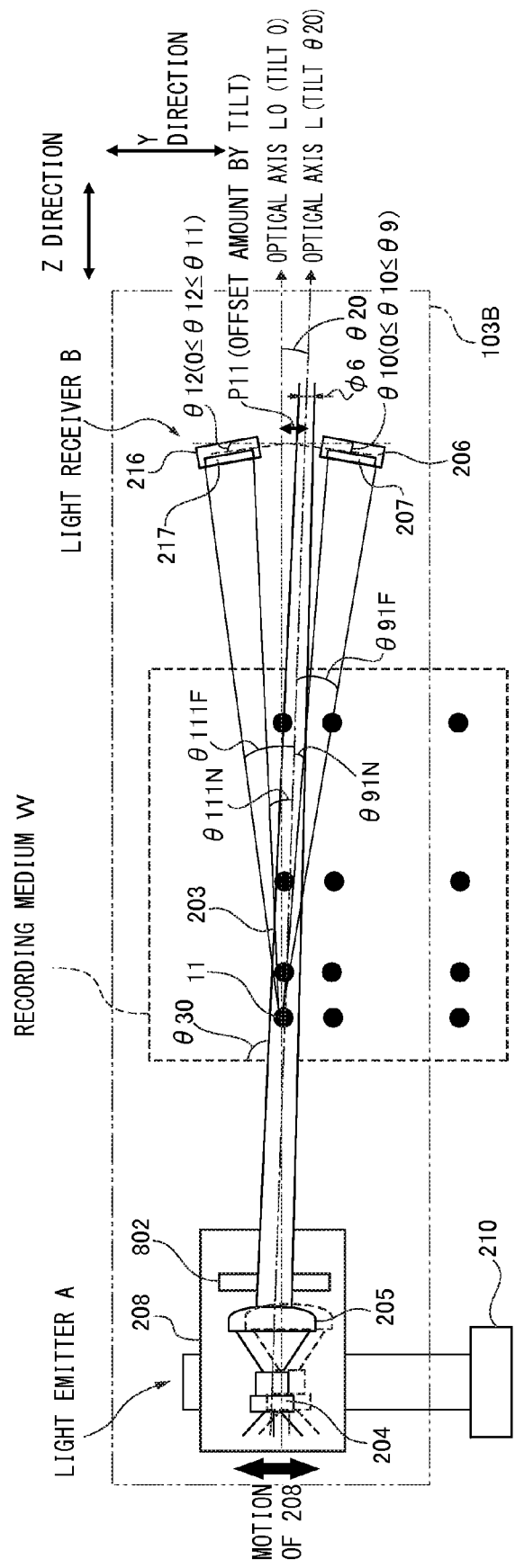
FIG. 12B is a schematic overhead view of the discharged liquid droplet detecting device according to the third embodiment by way of example.
Figure 12C:
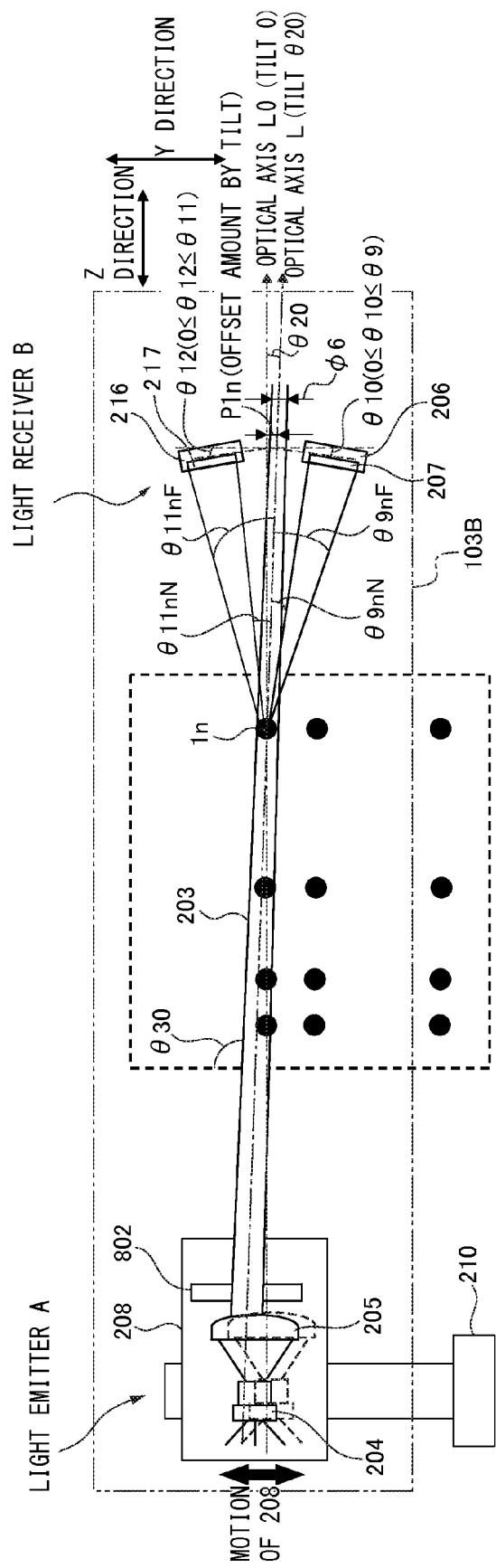
FIG. 12C is a schematic overhead view of the discharged liquid droplet detecting device according to the third embodiment by way of example.
Figure 12D:
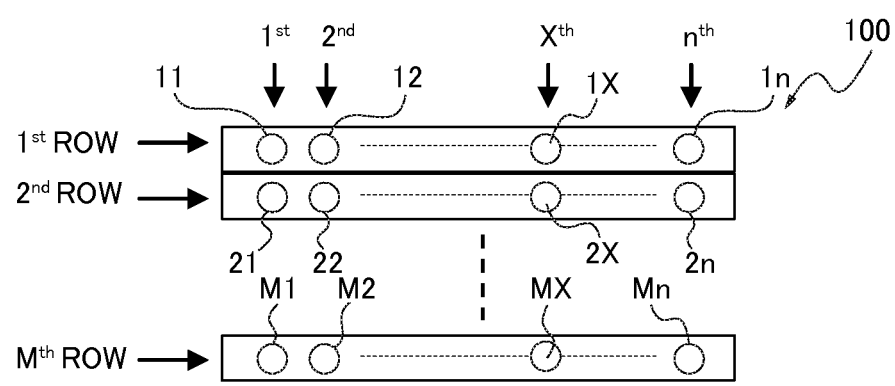
FIG. 12D is a schematic overhead semi-cross section view of the inkjet head according to the third embodiment by way of example.

FIG. 12B is a schematic overhead view of the discharged liquid droplet detecting device 103B when the optical axis L of the light beam 203 is on the first nozzle 11 of the first row. FIG. 12C is a schematic overhead view of the discharged liquid droplet detecting device 103B when the optical axis L of the light beam 203 is on the $n^{th}$ nozzle $1n$ of the first row. FIG. 12D is a schematic overhead semi-cross section view of the inkjet head 100.

The discharged liquid droplet detecting device 103B is different from the one 103A in the second embodiment in including a converge element 802 in place of the aperture 801 and their basic structures are the same. The converge element 802 is configured to convert a parallel light beam 203 to a converging light beam. In FIG. 12A to FIG. 12D $\phi 6$ represents the major beam diameter of the light beam 203 and $\phi 5$ represents the minor beam diameter thereof. Either of the beam diameters $\phi 5$, $\phi 6$ can be set to the major axis, both of them can be the same ($\phi 5 = \phi 6$), or the shape of the beam can be rectangular or not depending on various kinds of conditions. Such conditions include the wavelength and intensity distribution of the light beam 203, the interval between the nozzle rows, the shape and size of the ink droplet 202, the type and radiation angle of the light emitting element 204, the distance between the light emitting element 204 and the collimator lens 205, the distance between the light emitting element 204 and the ink droplet 202, the distance between the ink droplet 202 and the light receiving elements 206, 216, the position and size of the light receiving elements 206, 216, and the distance between the inkjet head 100 and a printing material (recording medium W). According to the third embodiment the converge element 802 is used to convert a parallel light beam to a converging light beam. However, the present invention should not be limited thereto. Alternatively, the light emitting element 204 and collimator lens 205 can be disposed with a larger distance to convert a parallel light beam to a converging light beam, for example, leading to further reducing manufacturing costs.

The two light receiving elements 206, 216 of the light receiver B are disposed outside the beam diameter $\phi 6$ of the light beam 203 so that their light receiving surfaces 207, 217 do not enter the beam diameter $\phi 6$. However, it is preferable to place the light receiving elements 206, 216 adjacent to the beam diameter $\phi 6$.

Further, the light receiving element 206 is disposed at angle $\theta 9$ relative to the optical axis L and at angle $\theta 10$ ($0 \leq \theta 10 < \theta 9$) relative to the vertical direction of the optical axis L. The angles $\theta 9$ and $10$ correspond to the angles $\theta 1$ and $\theta 2$ in the first embodiment. The other light receiving element 216 is disposed at angle $\theta 11$ relative to the optical axis L and at angle $\theta 12$ ($0 \leq \theta 12 < \theta 11$) relative to the vertical direction of the optical axis L. The angles $\theta 11$ and $12$ correspond to the angles $\theta 3$ and $\theta 4$ in the first embodiment.

The angles $\theta 9$ and $\theta 11$ have to be in a range of $\theta 9 > \theta 9$ min and $\theta 11 > \theta 11$ min which do not correspond to the above-mentioned conditions (1) and (2). The angles $\theta 9$ min and $\theta 11$ min are minimal angles between the light receiving elements 206 and 216 and the optical axis L, respectively.

The angle $\theta 9$ is represented as $\theta 91N$, $\theta 91F$, $\theta 9nN$, $\theta 9nF$ and the angle $\theta 11$ is represented as $\theta 111N$, $\theta 111F$, $\theta 11nN$, $\theta 11nF$ in FIGS. 12B and 12C. The angles $\theta 91N$ and $\theta 111N$ in FIG. 12B are angles between the optical axis L and a direction from the first nozzle 11 of the first row 1 to one ends of the light receiving elements 206, 216 close to the first row 1. The angle $\theta 91F$ and $\theta 111F$ are angles between the optical axis L and a direction from the first nozzle 11 of the first row 1 to the other ends of the light receiving elements 206 and 216 far to the first row. The angle $\theta 9nN$ and $\theta 11nN$ in FIG. 12C are angles between the optical axis L and a direction from the $n^{th}$ nozzle $1n$ of the first row 1 to one ends of the light receiving elements 206 and 216 close to the first row 1. The angles $\theta 9nF$ and $\theta 11nF$ are angles between the optical axis L and a direction from the first nozzle 11 of the $n^{th}$ row $1n$ to the other ends of the light receiving elements 206 and 216 far to the nozzle row 1.

According to the third embodiment the additionally provided converge element 802 can converge the light beam 203 and reduce the beam diameters $\phi 5$, $\phi 6$. The beam diameters $\phi 5$, $\phi 6$ are smaller than those $\phi 1$, $\phi 2$ in the first embodiment ($\phi 6 < \phi 2$, $\phi 5 < \phi 1$). As a result, the angles $\theta 9$, $\theta 11$ between the optical axis L and light receiving elements 206, 216 can be made smaller than the angles $\theta 1$, $\theta 3$ in the first embodiment.

As in the first and second embodiments, the discharged liquid droplet detecting device 103B can accurately detect a state of discharged ink droplets even with a tilt of the optical axis of light beam. The image forming device incorporating this device 103B can properly prevent operation stops and degradation of image quality. Further, the third embodiment can attain the following effects owing to the conversion of parallel light to converging light.

In the first and second embodiments in which the light beam 203 is parallel light, the amount of light emission of the light emitting element 204 is increased for the purpose of preventing attenuation of the maximal intensity of the light beam 203 by diffraction. Also, the moving unit 210 moves the light emitting unit 208 to an optimal position so that the center of the ink droplet 202 coincides with the position in which the intensity distribution of the light beam 203 reaches maximal.

Meanwhile, in the third embodiment using the converging light, the amount of the light beam 203 incident on the ink droplet 202 from each nozzle is increased from the nozzle 11 to the nozzle $1n$. This makes it possible to increase the amount of scattered light S received at the light receiving elements 206, 216 without increasing the light emission amount of the element 204 and moving the light emitting unit 208 as in the first and second embodiments. Thus, it is able to increase the amount of the scattered light S from the discharged ink droplet 202 received by the light receiving elements 206, 216 relative to the amount of noise light N (offset light). As a result, S/N ratio is enlarged, improving the accuracy at which the scattered light S is detected and more reliably detecting the state of discharged ink droplets 202.

Moreover, the influence from diffracted light is changed by changing the converging rate of the light beam 203 with the converge element 802 so that the scattered light amount from the ink droplet 202 is changed in accordance with a distance from the light receiving elements 206, 216. Taking this into account, the converging rate of the converge element 802 is set to an optimal value such that the minimal value of the scattered light amount of each ink droplet 202 is increased. Specifically, if a minimal amount of scattered light at a converging rate a is A and that at another converging rate β is B, the converging rate is set to a larger one of the minimal values A and B. With the minimal values A>B, the converging rate α is adopted. Thus, it is able to increase the amount of incident light on the ink droplet 202 and maintain the light receiving amount without an increase in the light emission amount. By use of converging light instead of parallel light, it is possible to lower the light emission amount of the light emitting element 204 while maintaining the detecting accuracy for discharged ink drops. Consequently, the durability of the light emitting element 204 can be enhanced by suppressing an increase in temperature thereof and electricity cost of the light emitting element 204 can be reduced.

Although the present invention has been described in terms of exemplary embodiments, it is not limited thereto. It should be appreciated that variations or modifications may be made in the embodiments described by persons skilled in the art without departing from the scope of the present invention as defined by the following claims.

For example, the respective elements of the image forming device and the discharged liquid droplet detecting device according to any of the above embodiment can be controlled by hardware, software, or a combination of both.

By use of software, a program containing processing sequences can be installed in a memory of a computer mounted in dedicated hardware or in a general-use computer on which various kinds of processing are executable.

For example, program can be pre-stored in hardware or ROM (Read Only Memory) as a recording medium. Also, program can be temporarily or permanently stored in a removable recording medium. Such a removable recording medium can be provided as packaged software. The recording medium includes a floppy® disc, CD-ROM (Compact Disc Read Only Memory), DVD (Digital Versatile Disc), magnetic disc, and semiconductor memory.

Further, program can be installed from such a removable recording medium to a computer, wirelessly transferred from a web site to a computer, or transferred to a computer via network.

The processing and operations of the image forming device and the discharged liquid droplet detecting device are executable not only in time series as described above but also depending on the operation performance of a device executing the processing or individually or in parallel when needed.

What is claimed is:

1. A device for detecting a state of a liquid droplet discharged from each of nozzles placed in one or more rows, comprising:
    a light emitting element to emit a light beam to the liquid droplet from a nozzle in question; and
    a pair of light receiving elements disposed on both sides of a beam diameter of the light beam via an optical axis to receive scattered light occurring from the liquid droplet for detecting a state of the discharged liquid droplet on the basis of the scattered light, wherein
    either of the pair of the light receiving elements is selected for receiving the scattered light from the liquid droplet discharged from the nozzle according to a positional relation between the nozzle and the pair of light receiving elements;
    one of the pair of light receiving element in a larger distance from the light beam is selected when distances from the nozzle and the pair of light receiving elements are larger than a certain value; and
    one of the pair of light receiving elements in a smaller distance from the light beam is selected when the distances from the nozzle and the pair of light receiving elements are equal to or smaller than the certain value.

2. The device according to claim 1, wherein
    the selected light receiving element is one disposed to receive an amount of noise light other than the scattered light equal to or smaller than a saturation limit value and an amount of the scattered light equal to or larger than a threshold.

3. The device according to claim 2, wherein
    when the amounts of noise light received by both of the pair of light receiving elements are equal to or smaller than the saturation limit value and the amounts of the scattered light are equal to or larger than the threshold, one of the light receiving element which receives a smaller amount of noise light is selected.

4. The device according to claim 1, further comprising
    an aperture for narrowing down the light beam emitted from the light emitting element.

5. The device according to claim 1, wherein
    the light beam emitted from the light emitting element is converted from a parallel beam to a converging beam.

6. The device according to claim 1, further comprising
    a mover to move the light emitting element in a direction crossing the optical axis of the light beam so as to emit the light beam to a liquid droplet discharged from the nozzle as a subject of detection.

7. The device according to claim 1, wherein
    when a number of the nozzle rows is M, M+1 light receiving elements are provided on both sides of each nozzle row, M being one or more integer.

8. The device according to claim 1, wherein
    when a number of the nozzle rows is M, M/2+1 light receiving elements are provided on both sides of every two adjacent nozzle rows, M being one or more integer.

9. An image forming device comprising the device according to claim 1.

10. A method for detecting a state of a liquid droplet discharged from each of nozzles placed in one or more rows, comprising:
    emitting the light beam to the liquid droplet discharged from a nozzle in question;
    receiving the scattered light occurring from the liquid droplet on a pair of light receiving elements disposed on both sides of a beam diameter of the light beam via an optical axis;
    selecting one of the pair of the light receiving elements which receives an amount of noise light other than the scattered light equal to or smaller than a saturation limit value and an amount of the scattered light equal to or larger than a threshold; and
    detecting a state of the liquid droplet on the basis of the amount of the scattered light received by the selected light receiving element.

11. A device for detecting a state of a liquid droplet discharged from each of nozzles placed in one or more rows, comprising:
    a light emitting element to emit a light beam to the liquid droplet from a nozzle in question; and
    a pair of light receiving elements disposed on both sides of a beam diameter of the light beam via an optical axis to receive scattered light occurring from the liquid droplet for detecting a state of the discharged liquid droplet on the basis of the scattered light, wherein
    either of the pair of the light receiving elements is selected for receiving the scattered light from the liquid droplet discharged from the nozzle according to a positional relation between the nozzle and the pair of light receiving elements; and the selected light receiving element is one disposed to receive an amount of noise light other than the scattered light equal to or smaller than a saturation limit value and an amount of the scattered light equal to or larger than a threshold.

12. The device according to claim 11, wherein the light beam emitted from the light emitting element is converted from a parallel beam to a converging beam.

13. The device according to claim 11, further comprising a mover to move the light emitting element in a direction crossing the optical axis of the light beam so as to emit the light beam to a liquid droplet discharged from the nozzle as a subject of detection.

14. The device according to claim 11, wherein when a number of the nozzle rows is M, M+1 light receiving elements are provided on both sides of each nozzle row, M being one or more integer.

15. The device according to claim 11, wherein when a number of the nozzle rows is M, M/2+1 light receiving elements are provided on both sides of every two adjacent nozzle rows, M being one or more integer.

16. An image forming device comprising the device according to claim 11.

* * * * *